US012788377B2

(12) United States Patent
Arrow et al.

(10) Patent No.: US 12,788,377 B2
(45) Date of Patent: *Nov. 10, 2026

(54) APPARATUSES AND METHODS FOR SEGREGATING TISSUE SAMPLES FOR MULTIPLE DIAGNOSTIC MODALITIES

(71) Applicant: Virchow Medical, Inc., San Diego, CA (US)

(72) Inventors: Alexander Arrow, Lakeside, CA (US); Wilfrido Mojica, Amherst, NY (US)

(73) Assignee: Virchow Medical, Inc.

( * ) Notice: Subject to any disclaimer, the term of this patent is extended or adjusted under 35 U.S.C. 154(b) by 113 days.

This patent is subject to a terminal disclaimer.

(21) Appl. No.: 18/952,403

(22) Filed: Nov. 19, 2024

(65) Prior Publication Data

US 2025/0160803 A1 May 22, 2025

Related U.S. Application Data

(63) Continuation-in-part of application No. 18/403,550, filed on Jan. 3, 2024, which is a continuation-in-part of application No. 18/514,870, filed on Nov. 20, 2023.

(51) Int. Cl.
*A61B 10/00* (2006.01)
*A61B 10/02* (2006.01)

(52) U.S. Cl.
CPC ...... *A61B 10/0096* (2013.01); *A61B 10/0275* (2013.01); *A61B 2010/0208* (2013.01)

(58) Field of Classification Search
None
See application file for complete search history.

(56) References Cited

U.S. PATENT DOCUMENTS 5,663,051 A 9/1997 Van Vlasselaer et al.
5,833,860 A * 11/1998 Kopaciewicz ..... B01J 20/28033 210/473
2003/0086830 A1 5/2003 Haywood et al.
2004/0005246 A1 1/2004 Efthimiadis et al.
2006/0037903 A1 * 2/2006 Smith ...................... G01N 1/40 210/240
2010/0248215 A1 * 9/2010 Halverson ................ G01N 1/38 435/235.1

(Continued)

OTHER PUBLICATIONS

International Search Report corresponding to PCT/US2025/055918 dated Mar. 25, 2026.

(Continued)

*Primary Examiner* — P. Kathryn Wright
(74) *Attorney, Agent, or Firm* — Spencer Fane, LLP

(57) ABSTRACT

Apparatuses and methods for recovering solid tissue and dislodged cells ("D-cells") from a biopsy are disclosed herein. In an embodiment, a biopsy container apparatus for recovering solid tissue and D-cells from a biopsy includes a buffer container, a sieve container and a sample collection container. The buffer container includes a buffer chamber. The sieve container is located least partially within the buffer container and includes a sieve surface configured to pass the D-cells from the biopsy but not the solid tissue from the biopsy into the buffer chamber. The sample collection container is removably attached to the buffer container and includes a reagent chamber.

20 Claims, 17 Drawing Sheets

(56) References Cited

U.S. PATENT DOCUMENTS

| | | | | |
|---|---|---|---|---|
| 2011/0146418 | A1* | 6/2011 | Brevnov | G01N 1/4005 73/863.23 |
| 2012/0053484 | A1 | 3/2012 | Parks | |
| 2012/0061392 | A1 | 3/2012 | Beach et al. | |
| 2012/0220044 | A1 | 8/2012 | Sharma et al. | |
| 2013/0095473 | A1 | 4/2013 | Groelz | |
| 2013/0295673 | A1 | 11/2013 | Taghizadeh et al. | |
| 2013/0345596 | A1 | 12/2013 | Zimmon | |
| 2015/0031040 | A1* | 1/2015 | Calanca | G01N 1/4077 435/6.12 |
| 2015/0056614 | A1 | 2/2015 | Mikolajczyk et al. | |
| 2015/0289856 | A1* | 10/2015 | Saqi | A61B 10/0096 422/534 |
| 2018/0361386 | A1* | 12/2018 | Hjelseth | B01L 3/561 |
| 2019/0185799 | A1* | 6/2019 | Katou | C12M 23/24 |
| 2019/0242798 | A1* | 8/2019 | Gellibolian | C12N 15/1017 |
| 2021/0079328 | A1 | 3/2021 | Barousse et al. | |
| 2024/0117406 | A1* | 4/2024 | Kawabe | B01L 3/5021 |
| 2024/0252155 | A1 | 8/2024 | Saqi et al. | |

OTHER PUBLICATIONS

International Search Report and Written Opinion issued Jan. 13, 2025 in corresponding International Application No. PCT/US2024/046776.

Mojica et al., Front-end genomics: using an alternative approach for the recovery of high-quality DNA from core needle biopsies, 70 J. Clinical Pathology 488 (Oct. 24, 2016).

Mojica et al., Core needle biopsy wash as a tool for acquiring additional diagnostic material for laboratory testing, J. Clinical Pathology (Online) (Mar. 1, 2021), https://jcp.bmj.com/content/75/5/345.

Padmanabhan et al., Improving Adequacy of Small Biopsy and Fine-Needle Aspiration Specimens for Molecular Testing by Next-Generation Sequencing in Patients with Lung Cancer, 141 Arch Pathol Lab Med 402 (Mar. 1, 2017).

Arshad et al., Cellular Material from Core Needle Biopsy Washes are Molecularly Representative of the Corresponding Parent Tissue that is Formalin Fixed and Paraffin Embedded (Poster) 111th Annual USCAP (Mar. 19, 2022).

* cited by examiner

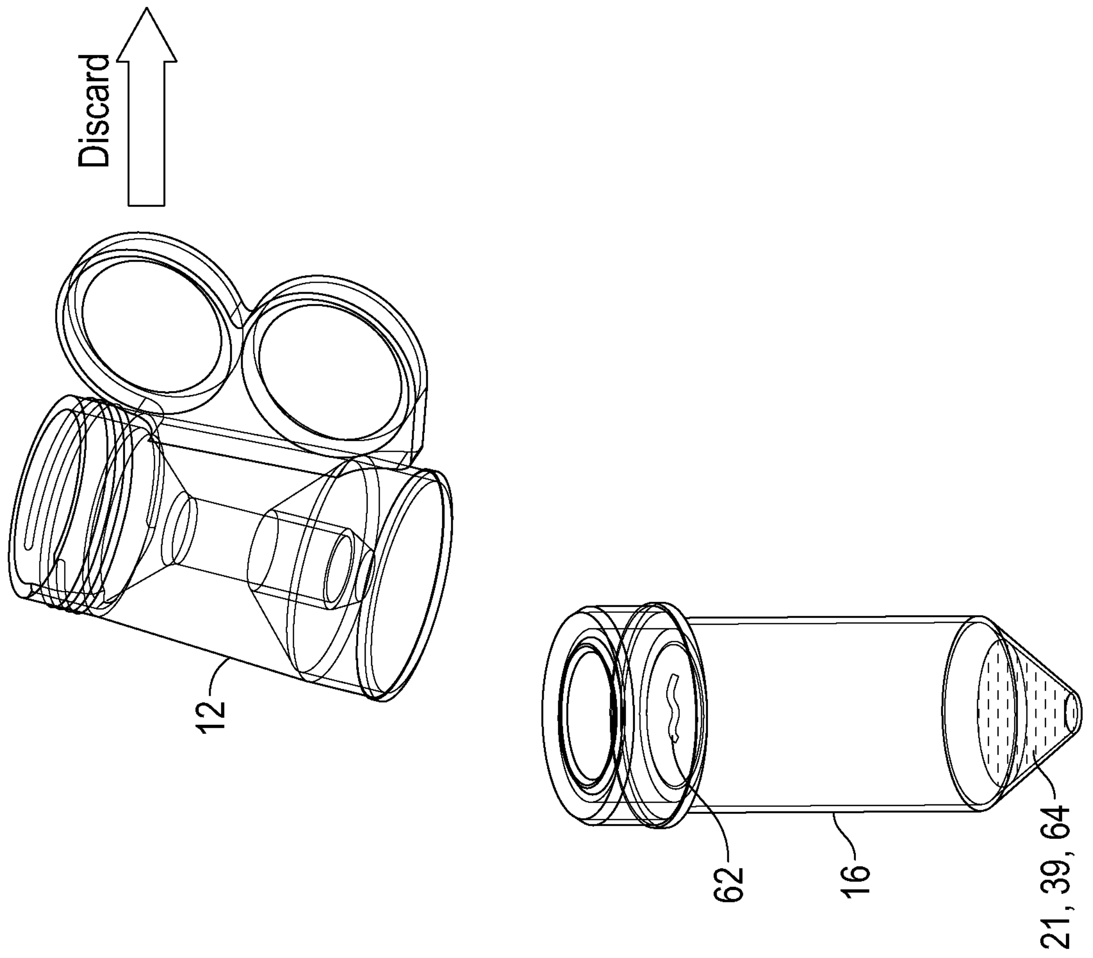
FIG. 14
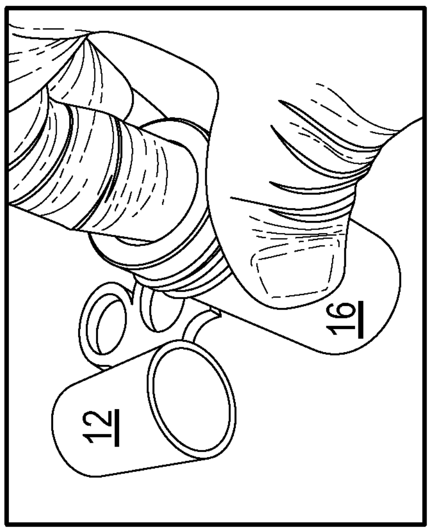

APPARATUSES AND METHODS FOR SEGREGATING TISSUE SAMPLES FOR MULTIPLE DIAGNOSTIC MODALITIES

PRIORITY

This application is a continuation-in-part of U.S. application Ser. No. 18/514,870, filed Nov. 20, 2023, entitled "Apparatuses and Methods for Segregating Tissue Samples for Multiple Diagnostic Modalities", and of U.S. application Ser. No. 18/403,550, filed Jan. 3, 2024, entitled "Apparatuses and Methods for Segregating Tissue Samples for Multiple Diagnostic Modalities", the entire contents of each of which are incorporated herein by reference.

BACKGROUND

Related Application

The apparatuses and methods of the present disclosure can be used in combination with the apparatuses and methods of U.S. patent application Ser. No. 18/468,416, filed Sep. 15, 2023, entitled "Methods and Systems for Recovering Assessable Analytes from Core Needle Biopsies," the entire contents of which is incorporated herein by reference.

Technical Field

The present disclosure generally relates to apparatuses and methods for segregating tissue samples for multiple diagnostic modalities. More specifically, the present disclosure relates to biopsy container apparatuses for recovering solid tissue and dislodged cells from a biopsy and their corresponding methods of use.

BACKGROUND INFORMATION

Solid tumor diagnostic procedures typically involve a tissue biopsy. Traditionally, a biopsy involves a substantial amount of tissue being surgically excised from a tumor or suspected affected tissue in a patient. The tissue, once removed from the patient's body, is processed and subsequently can be used for a number of different types of diagnostic tests.

In recent years, biopsy tools and techniques have advanced to be less invasive, with dramatically smaller tissue samples. Surgically-excised biopsies have largely been replaced by core needle biopsy (CNB) tools. Smaller biopsies are less traumatic for patients, quicker for the clinician to perform, and less expensive for the healthcare system in general. Hence, standard biopsy tissue size has declined significantly between the period before approximately 2010 and the years thereafter. The disadvantage of smaller biopsies is that they provide less tissue for pathologists to examine and analyze to render diagnostic opinions.

At the same time, diagnostic testing modalities have expanded to include an increased number of tests aimed at identifying molecular changes. The declining tissue biopsy size and the expanding quantity of testing required of the biopsied tissue has created an imbalance between tissue supply and demand. The result is that in some cases, clinicians make treatment decisions for patients with less diagnostic information than they would like. In other cases, patients are subjected to a second biopsy. The risk that a biopsy sample will have insufficient tissue to allow for the clinically-indicated tests to be performed is a big enough problem that it has several unofficial names, with "Tissue Exhaustion" being the most common. Tissue Exhaustion rates for core needle biopsies are reported in literature to be between 22-82% of all biopsies.

An imbalance therefore exists between the typical amount of tissue yielded from a CNB and the typical amount of tissue needed for testing. Healthcare quality is impacted by the shortfall in the quality and quantity of substrate available for molecular testing. This ultimately affects patient care, with many specimens received in the pathology laboratory not being available for molecular testing, resulting in these patients missing out on the improved treatment options associated with precision medicine (defined as using molecular testing to find a mutation to guide therapy).

It is unfortunate that standard tissue biopsy handling practices today result in some of the harvested cells being discarded along with medical waste. These cells come from the patient, unavoidably dislodged (referred to hereafter as D-cells) from the tissue due to the trauma associated with of the sharp edge of the CNB needle cutting through tissue and then pulling back into the metal CNB tube (e.g., as shown in FIGS. 8 and 9). These cells are not visible to the human eye. They contain valuable genetic information, but they are simply not noticed by the clinician or technician holding the CNB needle handle and placing the tissue into a standard formalin-containing cup-like container after harvesting then discarding the entire needle and any D-cells on it into a medical waste container. The current standard of care involves fixation of the tissue with formalin, in a process called formalin-fixation, paraffin embedding (FFPE), and which is known to create sub-optimal results when any tissue subjected to it is used as a substrate in molecular testing.

SUMMARY

The present disclosure provides a biopsy container apparatus that allows a clinician who performs a core needle biopsy to deposit the harvested tissue in such a way that it recovers cells that are dislodged ("D-cells") on the needle from the solid tissue that is procured during the biopsy procedure or from the patient's bodily tissue surrounding the pathway taken by the needle. D-Cells are an unrealized resource for diagnostic testing, mainly because cells are below the acuity of the human eye. This valuable biologic resource is typically discarded, but the apparatuses and methods of the present disclosure enable its recovery for diagnostic testing.

As discussed in more detail below, the biopsy container apparatus disclosed herein enables a clinician who performs a core needle biopsy to deposit the tissue in such a way that it contains and preserves the microscopic accompanying portions (D-cells) of the biopsied tissue that would otherwise be inadvertently discarded. More specially, the biopsy container apparatus disclosed herein enables cells that are dislodged from tissue that is procured during a biopsy procedure or from the patient's bodily tissue surrounding the pathway taken by the needle to be kept and segregated from the tissue that will be sent for standard pathology laboratory processing, using a specialized removable sieve suspended within a multi-functional watertight container. These recovered cells (D-cells) constitute an unrealized resource for diagnostic testing. This resource is typically discarded, but the apparatuses and methods of the present disclosure ensure recovery for diagnostic testing.

A first aspect of the present disclosure is to provide a biopsy container apparatus for recovering solid tissue and D-cells from a biopsy. The biopsy container apparatus includes a sample collection container, a basket sieve, and a buffer container. The sample collection container includes a reagent chamber. The basket sieve is configured for removable attachment at least partially within the sample collection container and includes a sieve surface configured to pass the D-cells from the biopsy but not the solid tissue from the biopsy. The buffer container is configured for removable attachment to the sample collection container and includes a buffer chamber.

A second aspect of the present disclosure is to provide another biopsy container apparatus for recovering solid tissue and D-cells from a biopsy. The biopsy container apparatus includes a sample collection container, a basket sieve, and a buffer container. The sample collection container includes a reagent. The basket sieve is configured for removable attachment at least partially within the sample collection container and includes a sieve surface configured to pass the D-cells from the biopsy but not the solid tissue from the biopsy. The buffer container is configured for removable attachment to the sample collection container and includes a buffer.

A third aspect of the present disclosure is to provide a method of recovering solid tissue and D-cells from a biopsy using a buffer container apparatus including a buffer container, a basket sieve and a sample collection container. The method includes depositing the solid tissue and the D-cells from the biopsy into a buffer solution within the buffer container, removing the buffer container from the basket sieve and the sample collection container, pouring the solid tissue, the D-cells and the buffer solution into the basket sieve while the basket sieve is located within the sample collection container, removing the basket sieve with the solid tissue from the sample collection container, placing the basket sieve with the solid tissue into a sealed container for tissue processing, and sealing a mixture including the D-cells, the buffer solution and the reagent for diagnostic testing.

A fourth aspect of the present disclosure is to provide another biopsy container apparatus for recovering solid tissue and D-cells from a biopsy. The biopsy container apparatus includes a buffer container, a sieve container and a sample collection container. The buffer container includes a buffer chamber. The sieve container is located at least partially within the buffer container and includes a sieve surface configured to pass the D-cells from the biopsy but not the solid tissue from the biopsy into the buffer chamber. The sample collection container is removably attached to the buffer container and includes a reagent chamber.

A fifth aspect of the present disclosure is to provide another biopsy container apparatus for recovering solid tissue and D-cells from a biopsy. The biopsy container apparatus includes a buffer container, a sieve container and a sample collection container. The buffer container includes a buffer solution. The sieve container includes a sieve surface positioned and configured to allow the D-cells but not the solid tissue from the biopsy to pass into the buffer solution in the buffer container. The sample collection is removably attached to the buffer container and includes a reagent.

A sixth aspect of the present disclosure is to provide a method of recovering solid tissue and D-cells from a biopsy using a buffer container apparatus. The method includes depositing the solid tissue and the D-cells from the biopsy into a sieve container while the sieve container is located at least partially within a buffer container which contains a buffer solution, placing the sieve container with the solid tissue into a sealed container for tissue processing, pouring the D-cells and the buffer solution from the buffer container into the sample collection container which contains a reagent, and sealing a mixture including the D-cells, the buffer solution and the reagent for diagnostic testing.

Other objects, features, aspects and advantages of the apparatuses and methods disclosed herein will become apparent to those skilled in the art from the following detailed description, which, taken in conjunction with the annexed drawings, discloses exemplary embodiments of the disclosed apparatuses and methods.

BRIEF DESCRIPTION OF THE DRAWINGS

Referring now to the attached drawings which form a part of this original disclosure:

FIG. 7 illustrates an example embodiment of a method of using the biopsy container apparatus of FIG. 1;

FIGS. 8 to 17 illustrate example embodiments of the steps of the method of FIG. 7;

FIG. 24 illustrates an example embodiment of a method of using the biopsy container apparatus of FIG. 21.

DETAILED DESCRIPTION OF EMBODIMENTS

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

Figure 3:
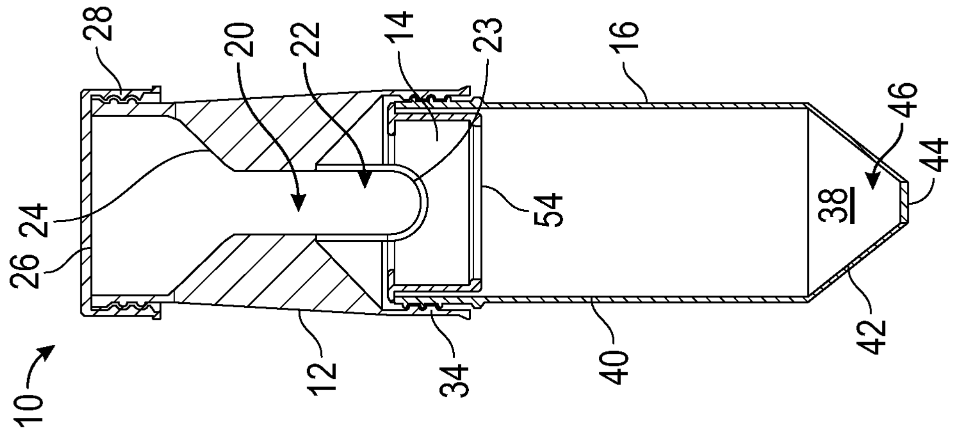
FIG. 3 illustrates a cross-sectional view of the biopsy container apparatus of FIG. 1 taken across section line III-III in FIG. 2.
Figure 2:
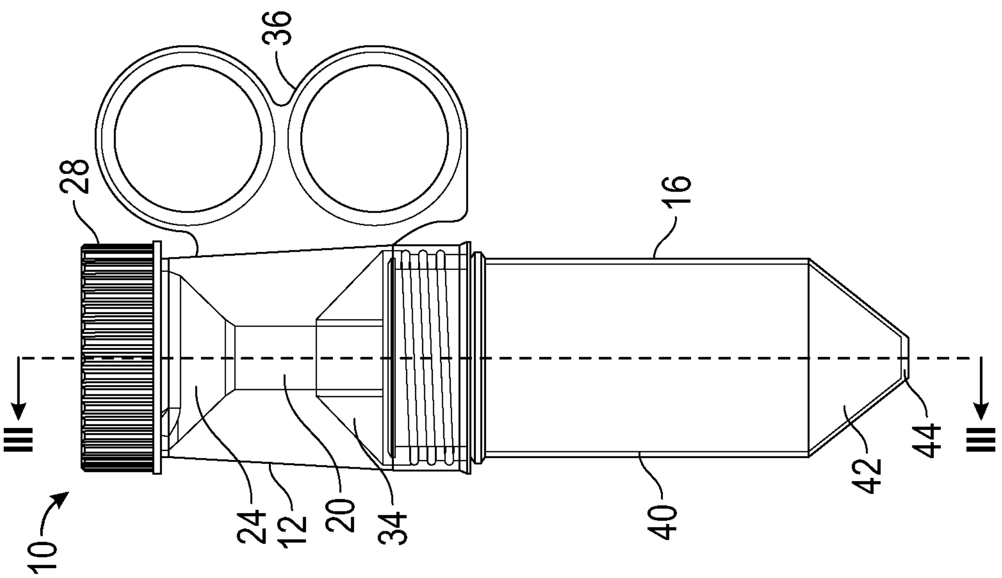
FIG. 2 illustrates a side view of the biopsy container apparatus of FIG. 1.
Figure 1:
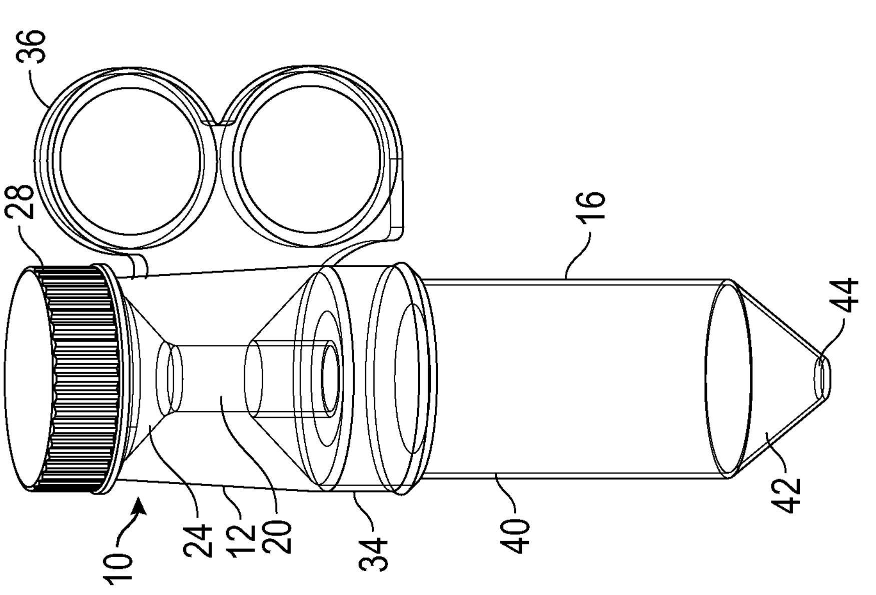
FIG. 1 illustrates a perspective view of an example embodiment of a biopsy container apparatus in accordance with the present disclosure.
Figure 4:
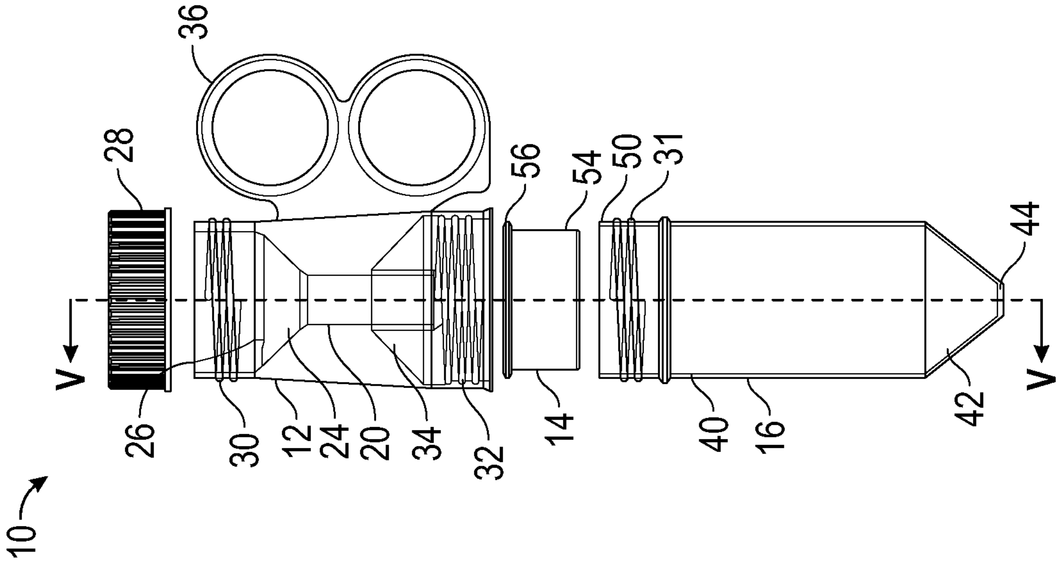
FIG. 4 illustrates an exploded view of the biopsy container apparatus of FIG. 1.
Figure 5:
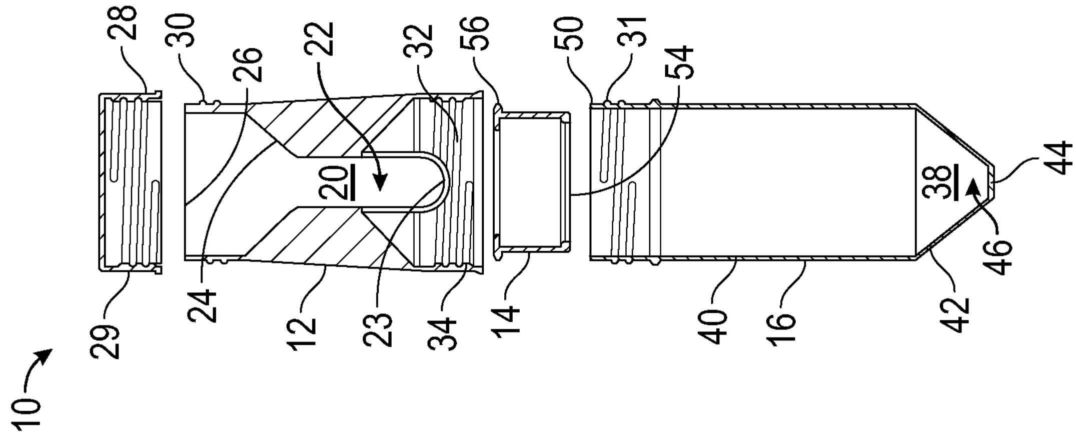
FIG. 5 illustrates a cross-sectional exploded view of the biopsy container apparatus of FIG. 1 taken across lines V-V in FIG. 4.

FIGS. 1 to 6 illustrate a first example embodiment of a biopsy container apparatus 10 for recovering solid tissue and D-cells from a biopsy in accordance with the present disclosure. In the illustrated embodiment, the biopsy container apparatus 10 includes a buffer container 12, a basket sieve 14 (also be referred to as a "sieve container") and a sample collection container 16, which are three separable elements that can be attached prior to a biopsy and then separated during the method of use disclosed herein. As illustrated, the buffer container 12 and basket sieve 14 are configured for removable attachment to the sample collection container 16. FIGS. 1 to 3 illustrate the buffer container 12, the basket sieve 14 and the sample collection container 16 attached together, while FIGS. 4 and 5 show the buffer container 12, the basket sieve 14 and the sample collection container 16 detached from each other.

The buffer container 12 includes a buffer chamber 20 for storing or receiving buffer solution 21. The bottom edge 23 of the buffer chamber 20 is sealed and watertight so that the inner space 22 of the buffer chamber 20 retains the buffer solution 21. In an embodiment, the buffer chamber 20 is pre-filled with the buffer solution 21 within the inner space 22. In an embodiment, the buffer solution 21 is a sterile phosphate-buffered saline (PBS) buffer solution. In an embodiment, the buffer chamber 20 includes between 2 and 4 mL of buffer solution. In an embodiment, the buffer chamber 20 is pre-filled with approximately 2-4 mL of buffer solution. While PBS is the most likely choice of buffer, any similar buffer solution, such as Buffer Roswell Park Memorial Institute ("RPMI 1640 Media") Buffer Solution, would serve the same purpose.

In the illustrated embodiment, the buffer container 12 includes a funnel to assist a user in depositing a biopsy sample from a core needle into the buffer solution 21 within the buffer chamber 20. More specifically, the buffer container 12 includes a funnel portion 24 leading into the buffer chamber 20. The funnel portion 24 flares outwardly from bottom to top, while the buffer chamber 20 has a generally cylindrical shape for insertion into the basket sieve 14 and/or the sample collection container 16 as shown in FIG. 3. The funnel portion 24 is configured to guide the solid tissue and the D-cells from the biopsy into the buffer chamber 20 when ejected from a core needle, as discussed in more detail below.

Figure 17:
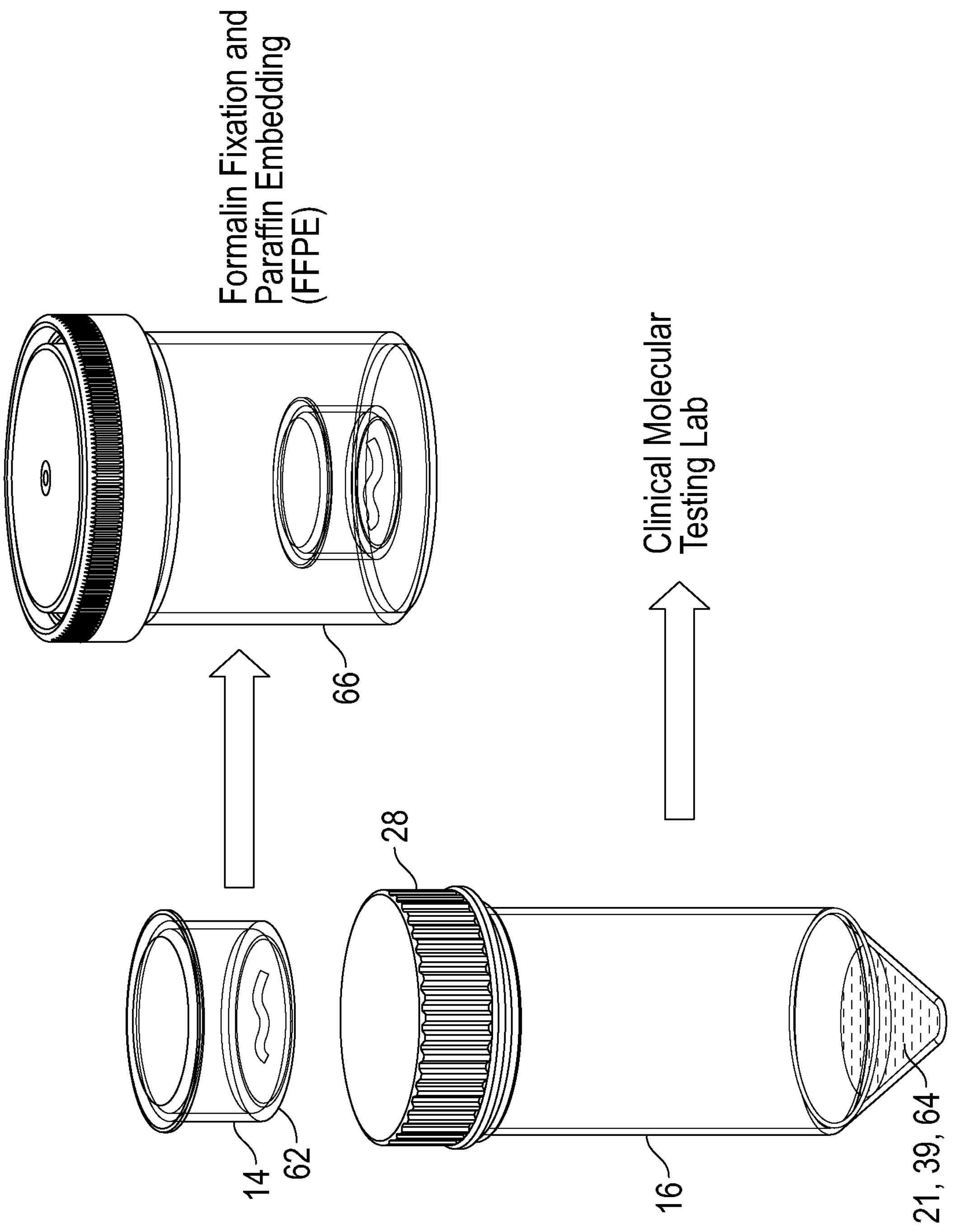

In the illustrated embodiment, the buffer container 12 includes a top opening 26 and a lid 28. The lid 28 attaches at or near the top of the funnel portion 24 to cover the top opening 26 and enclose the inner space 22 so that the buffer solution 21 does not spill if the biopsy container apparatus 10 is inverted. The lid 28 can be attached by being screwed onto the buffer container 12 at or near the top of the funnel portion 24, or by another suitable attachment mechanism. In the illustrated embodiment, the lid 28 is configured to attach to both the buffer container 12 and the sample collection container 16, so that a user can remove the lid 28 from the buffer container 12 when beginning use of the biopsy collection apparatus 10 and then later place the lid 28 on the sample collection container 16 to seal its contents, as shown in FIG. 17.

In the illustrated embodiment shown in FIGS. 4 and 5, the lid 28 includes a first attachment mechanism 29 to enable removable attachment to a second attachment mechanism 30 of the buffer container 12. As seen in FIG. 17, the first attachment mechanism 29 also enables removable attachment to a third attachment mechanism 31 of the sample collection container 16, enabling the lid 28 to be attached to the sample collection container 16 after being removed from the buffer container 12. In the illustrated embodiment, the buffer container 12 also includes a fourth attachment mechanism 32 to enable removable attachment to the third attachment mechanism 31 of the sample collection container 16. In the illustrated embodiment, the inner surface of the lid 28 includes the first attachment mechanism 29, the outer surface of the buffer container 12 includes the second attachment mechanism 30, the outer surface the sample collection container 16 includes the third attachment mechanism 31, and the inner surface of the buffer container 12 includes the fourth attachment mechanism 32. When attached as shown in FIGS. 1 to 3, the first attachment mechanism 29 and the second attachment mechanism 30 create a watertight seal between the buffer container 12 and the lid 28, and the third attachment mechanism 31 and the fourth attachment mechanism 32 create a watertight seal between the buffer container 12 and the sample collection container 16, so that liquid will not spill from the buffer container 12 or the sample collection container 16 if the biopsy container apparatus 10 is inverted. When attached as shown in FIG. 17, the first attachment mechanism 29 and the third attachment mechanism 31 create a watertight seal between the lid 28 and the sample collection container 16 so that liquid will not spill from the sample collection container 16 if the biopsy container apparatus 10 is inverted In the illustrated embodiment, the attachment mechanisms 29, 30, 31, 32 are screw threads. The screw threads of the first attachment mechanism 29 and the fourth attachment mechanism 32 have approximately the same size, and the screw threads of the second attachment mechanism 30 and the third attachment mechanism 31 have approximately the same size. Those of ordinary skill in the art will recognize from this disclosure that other attachment mechanisms are possible.

In the illustrated embodiment, the buffer container 12 includes a skirt 34 with the fourth attachment mechanism 32 on its inner surface. As seen in FIGS. 3 and 5, the skirt 34 encircles the buffer chamber 20. The buffer container 12 also includes a handle 36 protruding from the skirt 34. The handle 36 enables the user to (i) hold the biopsy container apparatus 10 with one hand while the other hand unscrews the lid 28, (ii) hold the biopsy container apparatus 10 steady with one hand while the other hand operates a core needle 60 containing a tissue sample, maneuvering it into the funnel portion 24 and depositing its contents therein, (3) unscrew the buffer container 12 from the sample collection container 16, and (4) lift and pour the contents of the buffer container 12 (e.g., solid tissue 62, D-cells 64 and buffer solution 21) into the basket sieve 14 and sample collection container 16.

The sample collection container 16 includes a reagent chamber 38 for storing or receiving a reagent 39. In FIG. 3, the sample collection container 16 includes an upper portion 40 and a lower portion 42, with the reagent chamber 38 located within and/or formed by the lower portion 42. The bottom edge 44 of the sample collection container 16 is sealed and watertight so that the reagent chamber 38 retains the reagent 39. In an embodiment, the reagent chamber 38 is pre-filled with the reagent 39 within the inner space 46. In an embodiment, the reagent 39 is a solution for lysing cells and preserving nucleic acids that is approximately 2× the normal concentration of an off-the-shelf cell lysing reagent. In an embodiment, the reagent 39 is Zymo DNA/RNA Shield™ reagent, or an equivalent for lysing cells and preserving nucleic acids which is 2× the normal concentration defined by and provided by Zymo. In an embodiment, the reagent chamber 38 includes between 2 and 4 mL of reagent 39. In an embodiment, the reagent chamber 38 is pre-filled with 2-4 mL of double-concentration cell lysis/nucleic acid stabilization reagent 39. In an embodiment, the reagent chamber 38 includes a first amount of reagent 39, and the buffer chamber 20 includes a second amount of buffer solution 21 that is approximately equal in volume to the first amount of reagent.

Figure 6:
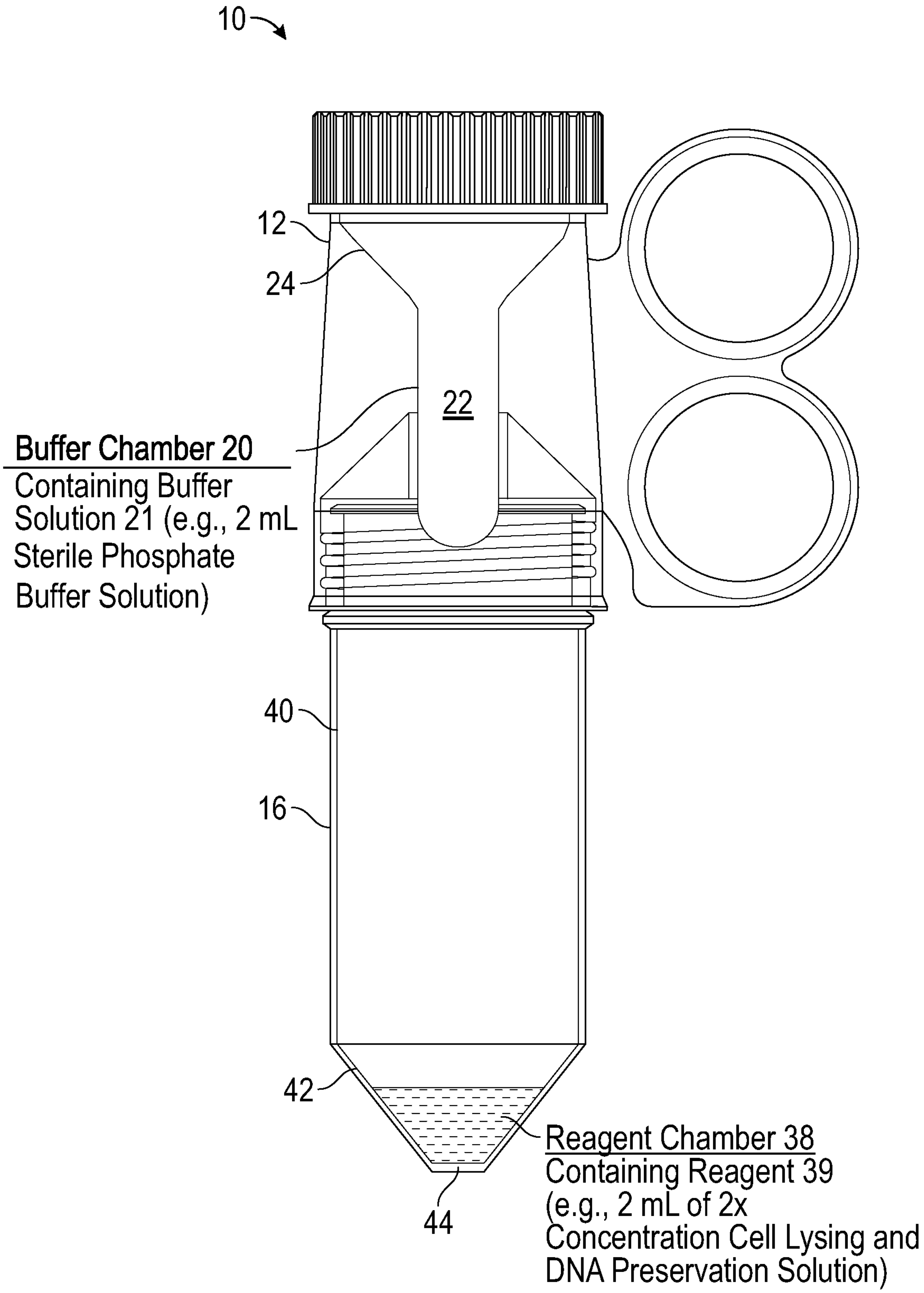
FIG. 6 illustrates an informational view of the biopsy container apparatus of FIG. 1.
Figure 9:
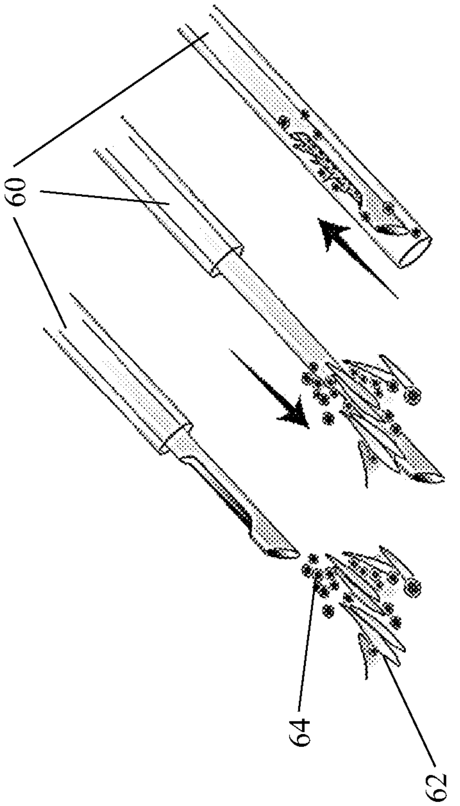
Figure 8:
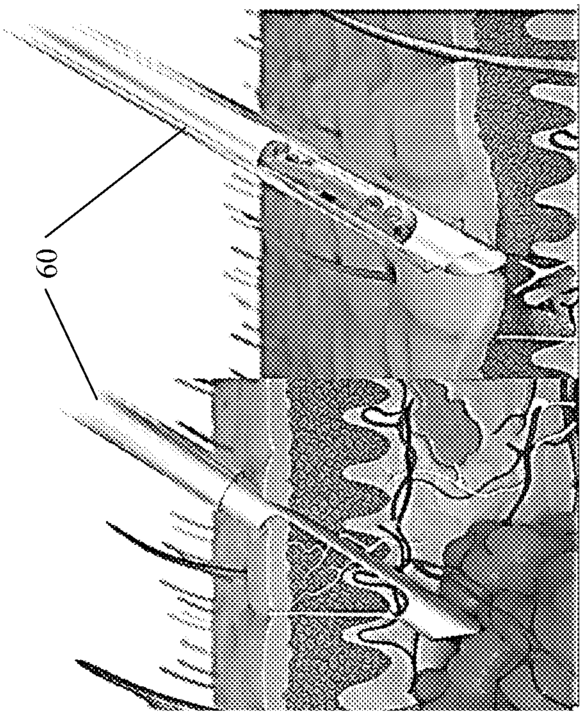
Figure 10:
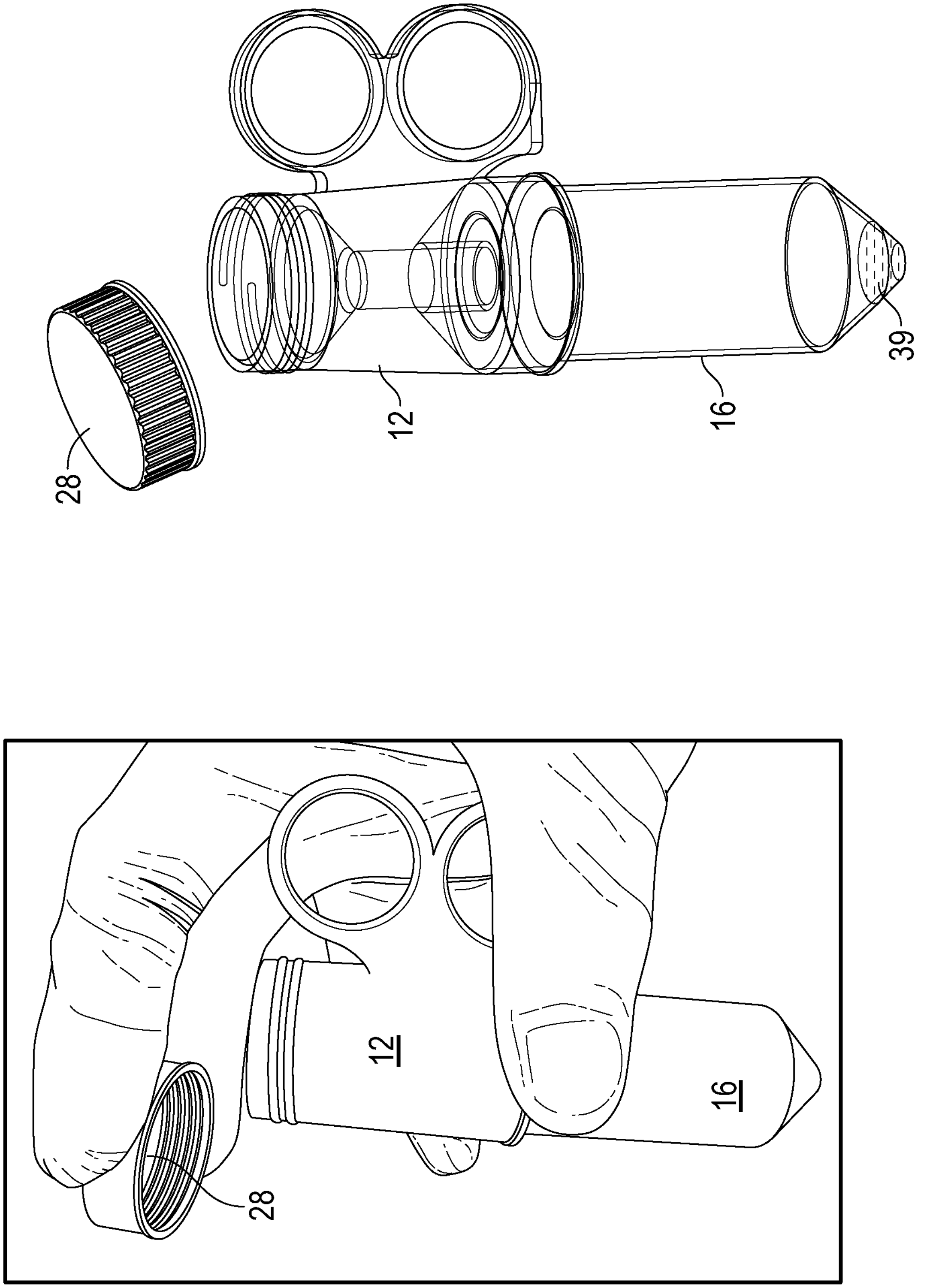
Figure 11:
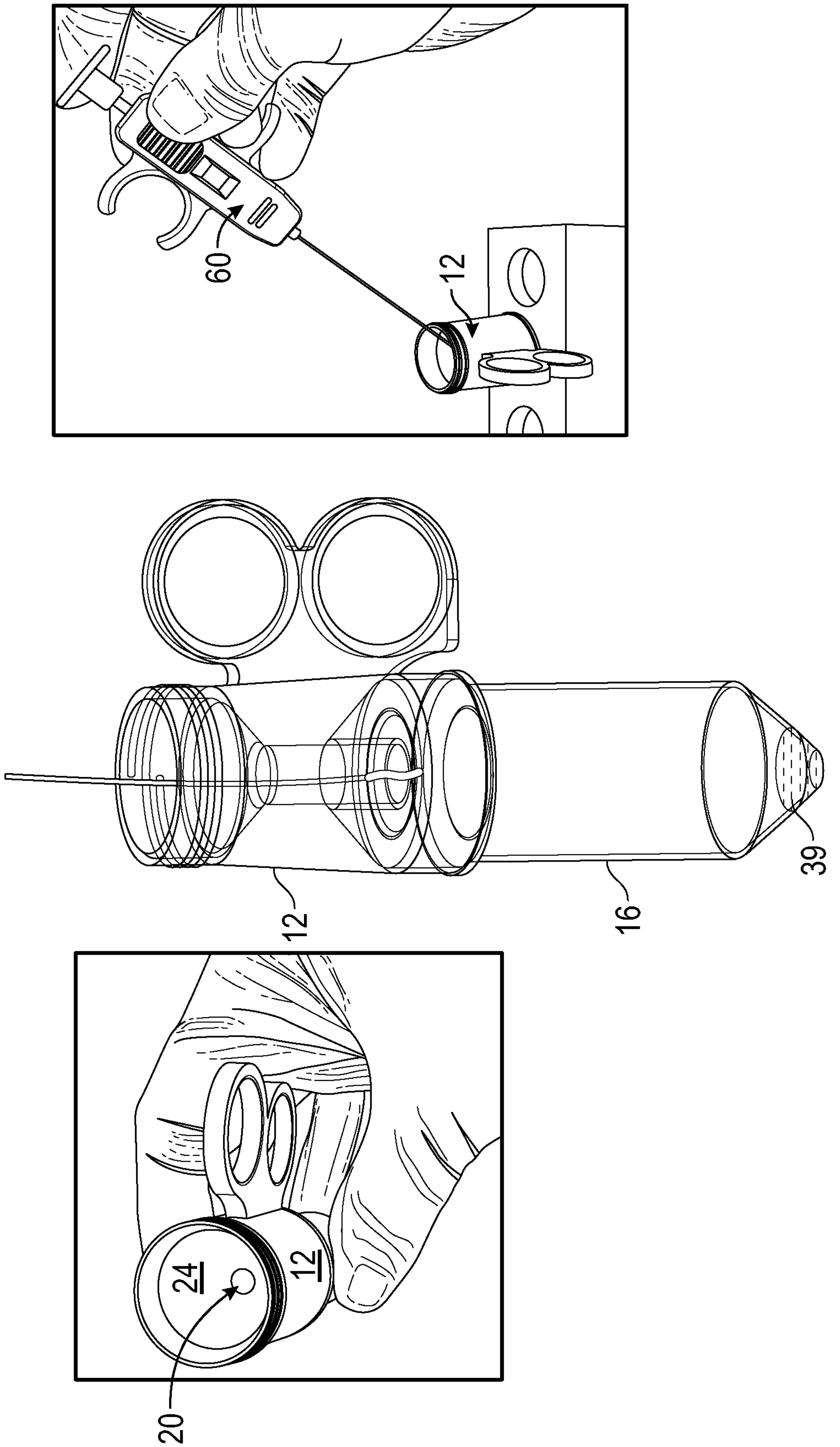
Figure 12:
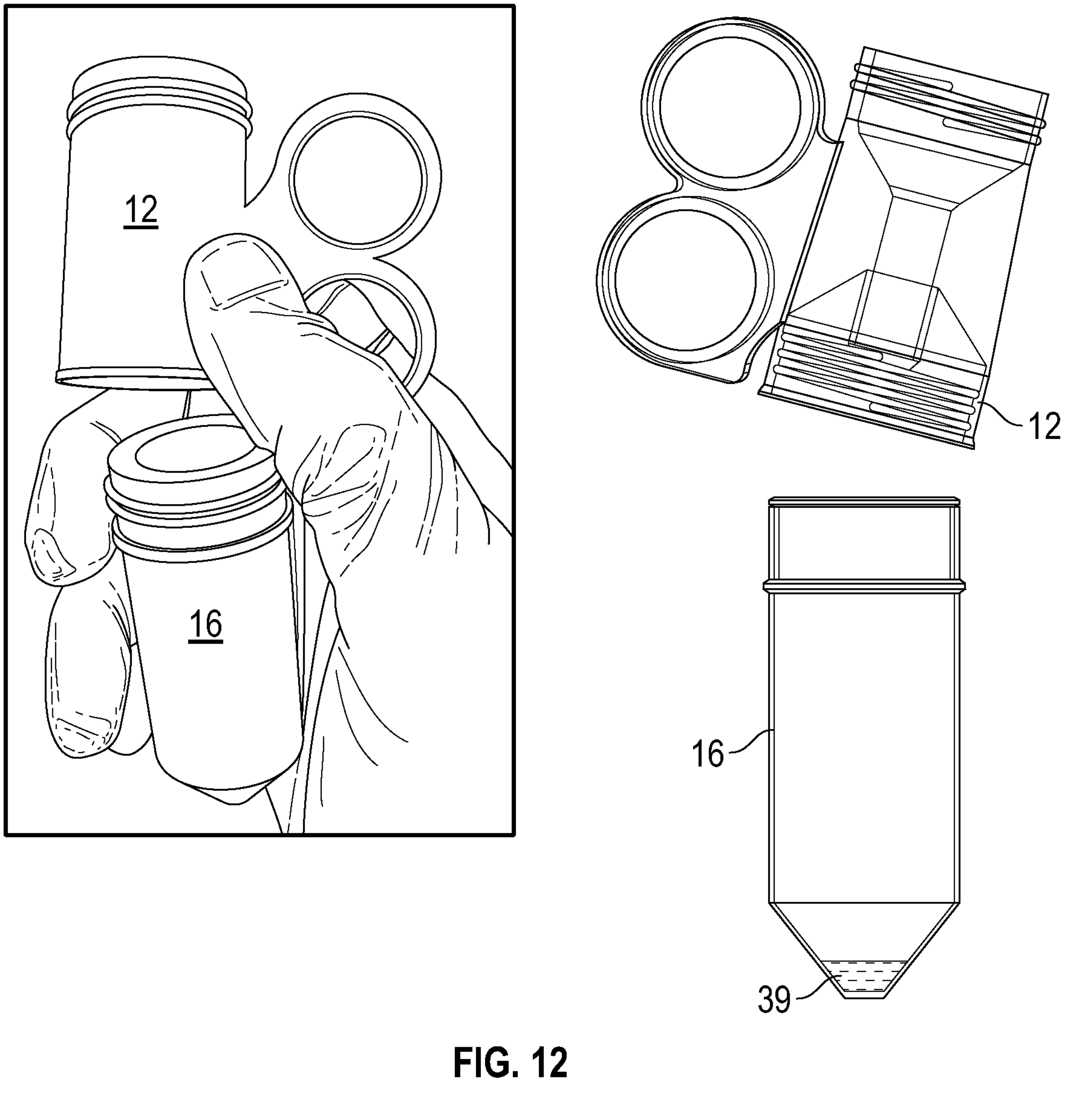

In the illustrated embodiment, the upper portion 40 of the sample collection container 16 is cylindrical, and the lower portion 42 of the sample collection container 16 tapers inwardly from top to bottom, with the lower portion 42 near the bottom edge 44 having a smaller inner diameter than the upper portion 40. As seen in FIGS. 5 and 6, the upper portion 40 of the sample collection container 16 includes a rim 50 configured to support the basket sieve 14. In an alternative embodiment, the upper portion 40 and the lower portion 42 can be approximately the same diameter, and the sample collection container 16 can include an internal ridge line within or between the upper portion 40 and the lower portion 42 which is configured to support the basket sieve 14.

The basket sieve 14 includes a sieve surface 54 configured to pass the D-cells from a biopsy but not solid tissue from the biopsy. The pore size of the sieve is approximately 350 microns in diameter per pore (the pore aperture size), or within a range of about 80 microns to 500 microns in diameter per pore (the pore aperture size) to allow D-cells to fall through. In the illustrated embodiment, the sieve surface 54 is the lower surface of the basket sieve 14. As seen in FIGS. 4 and 5, the basket sieve 14 also includes a lip 56 sized to rest on the rim 50 of the sample collection container 16 so that the basket sieve 14 is suspended within the sample collection container 16 above the reagent chamber 38 and below the buffer chamber 20 when the biopsy container apparatus 10 is assembled as shown in FIG. 3. In an alternate example embodiment, the basket sieve 14 can include loop-like or hook-like vertical members to assist a user in lifting the basket sieve 14 upward to remove the basket sieve 14 (and the tissue it carries) from the sample collection container 16 during use. As seen in FIG. 17, the basket sieve 14*c* is sized and shaped to be sealed within a corresponding specimen cup 66 and sent to a tissue pathology lab.

As seen in FIG. 3, when the buffer container 12, the basket sieve 14 and the sample collection container 16 are attached to each other, the basket sieve 14 is suspended above the reagent chamber 38 of the sample collection container 16, and the buffer chamber 20 is suspended above sieve surface 54 by attachment of the third attachment mechanism 31 to the fourth attachment mechanism 32. Those of ordinary skill in the art will recognize from this disclosure that there are other ways of attaching and/or arranging the elements besides as shown in the example embodiment of FIGS. 1-6.

As also seen in FIG. 3, when the basket sieve 14 is attached to the sample collection container 16, the basket sieve 14 is located at least partially within the sample collection container 16. In FIG. 3, the basket sieve 14 is located almost entirely within the sample collection container 16 besides the lip 56 protruding from the top of the sample collection container 16. Similarly, the buffer container 12 can be located at least partially or fully within the sample collection container 16 when attached to the sample collection container 16. In FIG. 3, the buffer container 12 is located partially within the sample collection container 16, with the reagent chamber 20 located partially within the sample collection container 16 but the funnel portion 24 located outside of the sample collection container 16. More specifically, the buffer chamber 20 of the buffer container 12 is at least partly located within the sample collection container 16, and the funnel portion 24 of the buffer container 12 is at least partially located outside of the sample collection container 16. Those of ordinary skill in the art will recognize from this disclosure that there are various ways to arrange the buffer container 12, the basket sieve 14 and the sample collection container 16 besides as shown in the example embodiment of FIGS. 1-6. In other embodiments, the buffer container 12 and/or basket sieve 14 can be removably attachable outside of the sample collection container 16.

The dimensions of a biopsy container apparatus 10 in accordance with the present disclosure can vary. In FIGS. 1 to 3, the total height of the biopsy container apparatus 10 is approximately 12.4 cm, the height of the sample collection container 16 is approximately 7.6 cm, the outer diameter of the upper portion 40 of the sample collection container 16 is approximately 3.0 cm, the outer diameter of the basket sieve 14 is approximately 2.7 cm with the rim 56 having an outer diameter of approximately 2.9 cm, and the outer diameter of the lid 28 is approximately 3.3 cm. Referring to FIGS. 3 and 5, the buffer chamber 20 has an approximate inner diameter of 10 mm and an approximate height of 30 mm. Those of ordinary skill in the art will recognize from this disclosure that these dimensions are an example only and can change with different embodiments.

Figure 18:
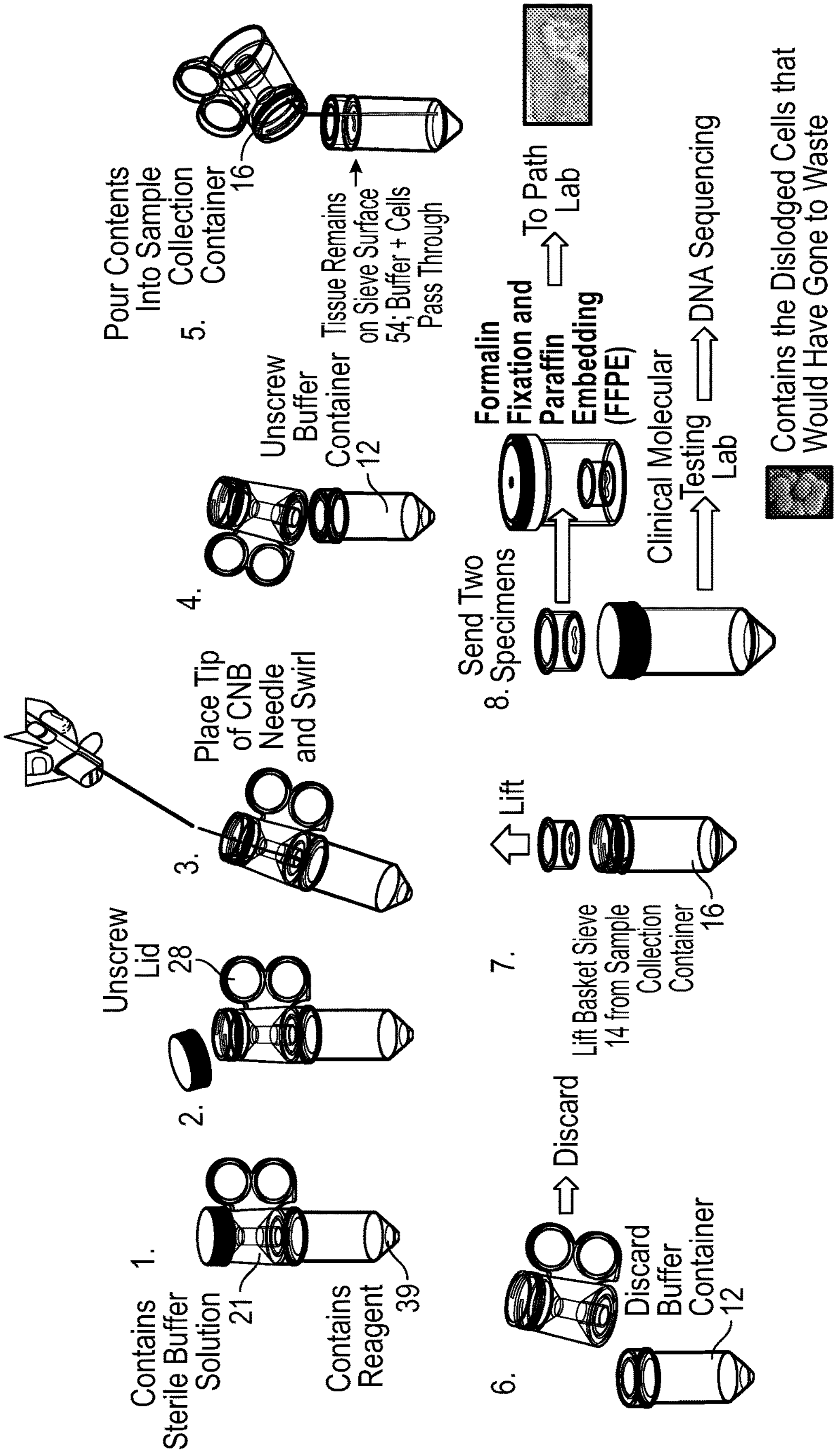
FIG. 18 illustrates a pictorial summary of the method of FIG. 7.

FIG. 7 shows an example embodiment of a method 100 of recovering solid tissue and D-cells from a biopsy using a biopsy container apparatus 10 in accordance with the present disclosure. FIGS. 8 to 17 illustrate various steps of the method 100, and FIG. 18 illustrates an example pictorial summary of the method 100. Those of ordinary skill in the art will recognize from this disclosure that certain steps can be added, removed or altered without departing from the spirit and scope of the present disclosure.

At step 102 (FIGS. 8 and 9) a user (e.g., interventional radiologist or other clinical user) uses a core needle 60 to harvest an image guided biopsy from a patient with suspicious mass lesion inside his or her body (e.g., liver, lung, kidney, etc). The core needle 60 removes both solid tissue 62 and dislodged cells 64 (D-cells) from the patient.

At step 104, (FIG. 10), the user removes the lid 28 from the buffer container 12. The lid 28 can be set aside and later reused to seal the sample collection container 16 at step 118.

At step 106 (FIG. 11), the user deposits the contents of the core needle 60 including the solid tissue 62 and the D-cells 64 into the buffer solution 21 within the buffer-buffer chamber 20. The user may swirl the CNB needle tip to deposit the harvested tissue sample by moving the needle in a roughly circular fashion in the closed distal end of the funnel shape 24, somewhat like the motion one would use with a manual egg beater, if the egg beater were a hollow-bore needle. The funnel portion 24 makes it easy for the user to spatially coordinate the CNB needle tip and the target area and provides a convenient way to for the user to place the tip of the needle (and therefore the tissue sample) near or into the buffer solution 21. That is, the larger funnel shape 24 of the present disclosure makes the buffer chamber 20 easier to hit since the user's hand is approximately eight (8) inches away from the needle tip (holding the handle; not the tip), and the other hand is holding the buffer container 12 or a conventional tray or rack in which the buffer container 12 is placed (not pictured) or otherwise unavailable and generally not used to guide the tip of the needle.

At step 108 (FIG. 12), the user removes the buffer container 12 from the sample container 16. The user removes the buffer container 12 from the sample collection container 16, for example, by detaching (e.g., unscrewing) the third attachment mechanism 31 and the fourth attachment mechanism 32.

Figure 13:
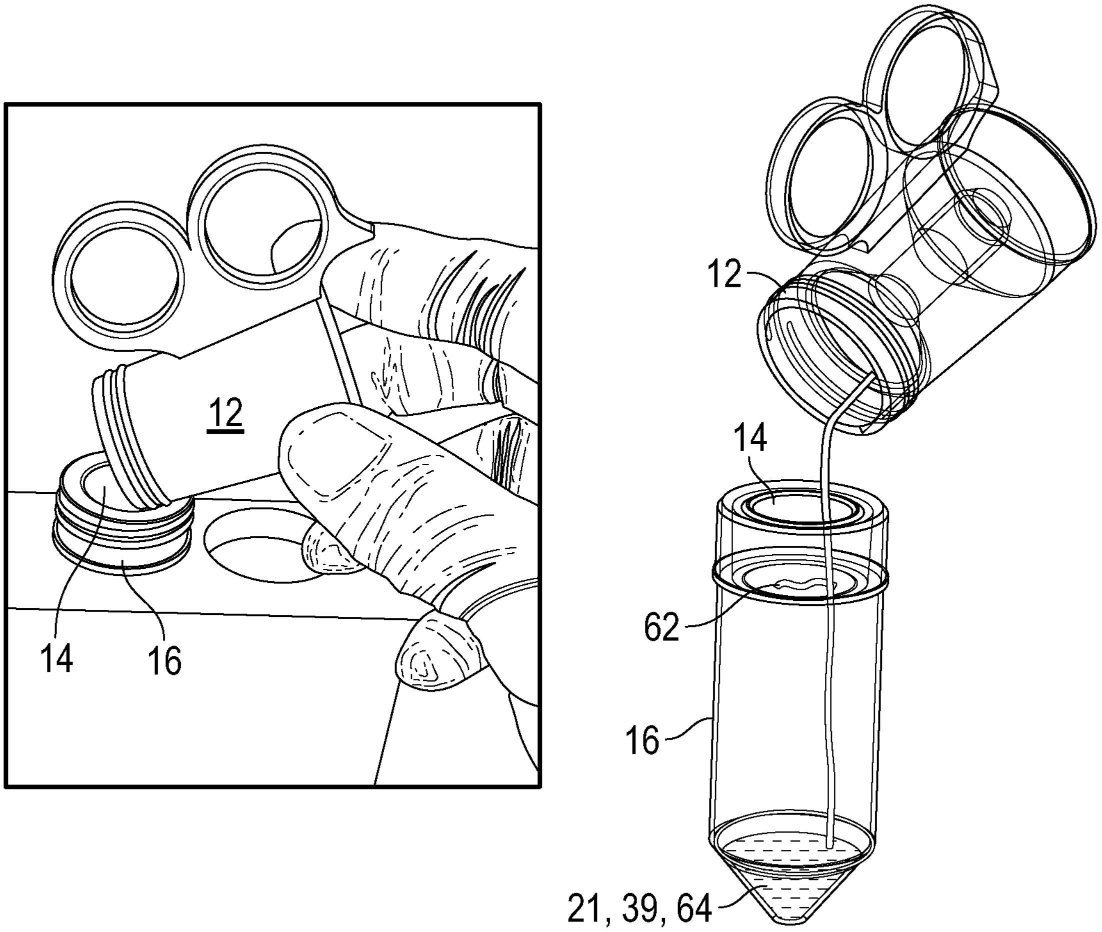
Figure 15:
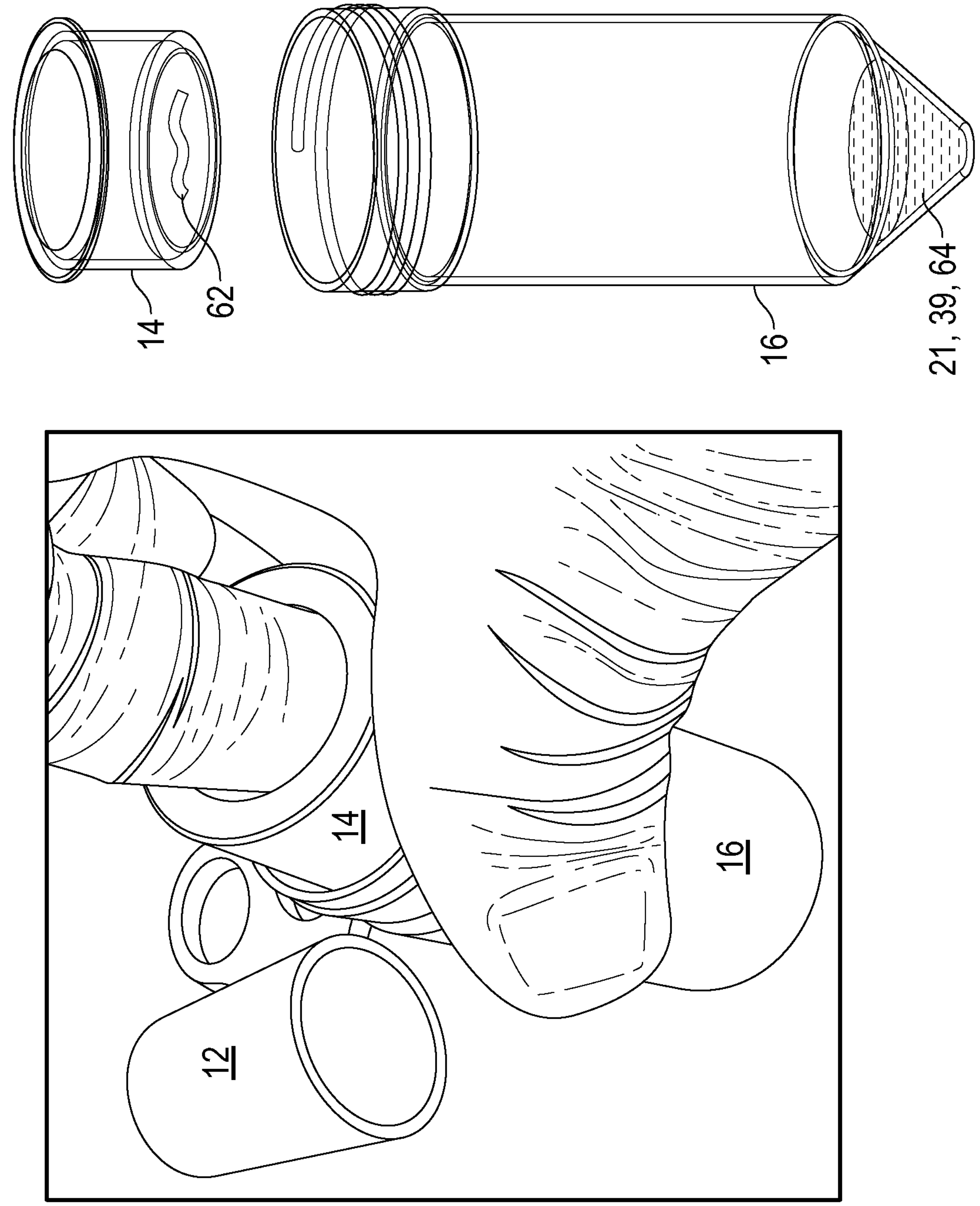
Figure 16:
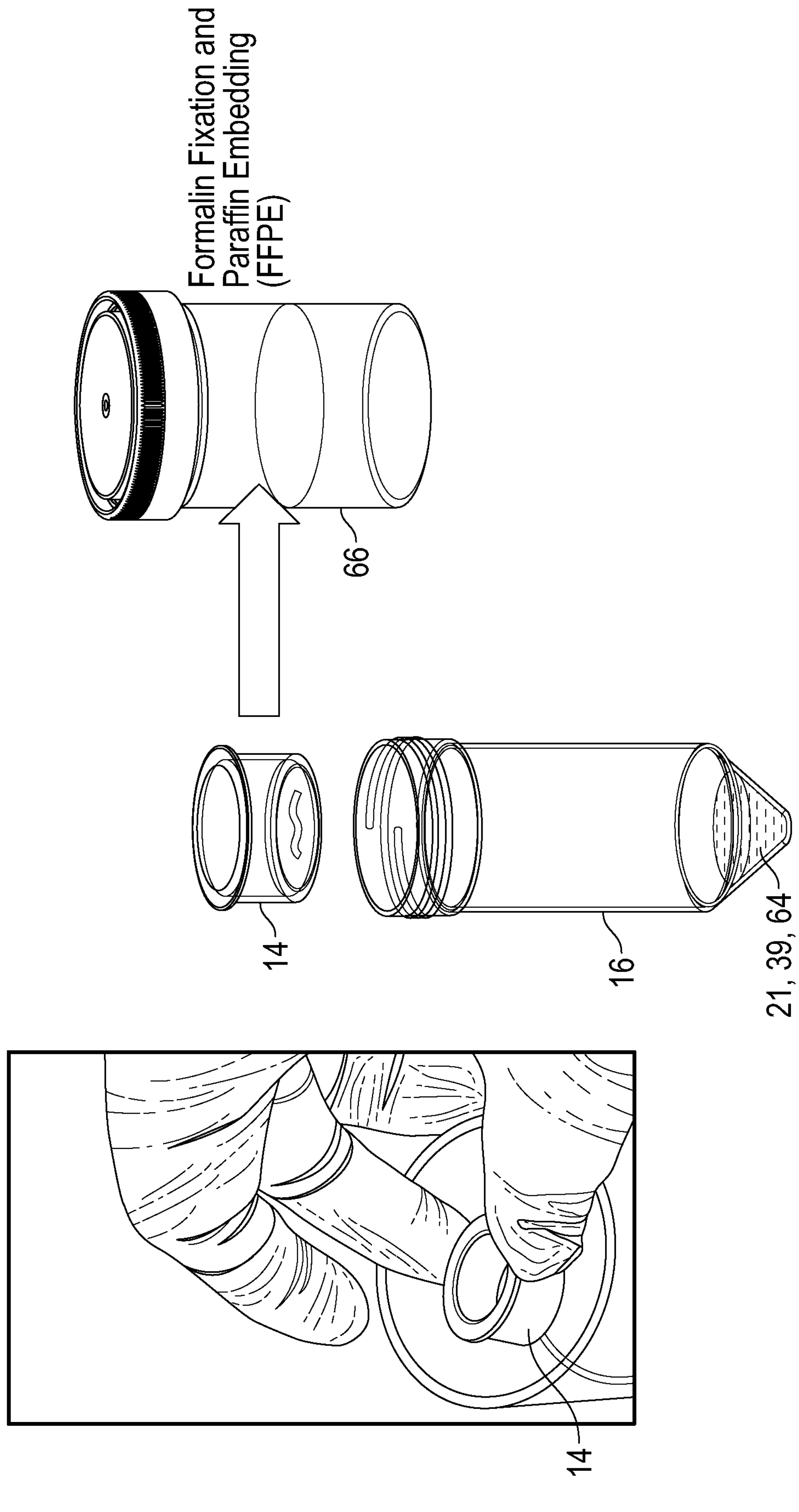

At step 110 (FIG. 13), the user pours the contents of the buffer container 12 (the solid tissue 62, the D-cells 64 and the buffer solution 21) into the basket sieve 14 that is located within the sample collection container 16. As seen in FIG. 13, the solid tissue 62 is captured by the sieve floor 54 and remains within the basket sieve 14, while the buffer solution 21 and the D-cells 64 fall through the sieve floor 54 and mix with the reagent 39 in the reagent chamber 38 of the sample collection container 16. Since the reagent 39 is 2× concentrated, the additional volume of buffer solution 21 and dislodged cells 64 restores the reagent concentration to normal.

At step 112, (FIG. 14), the user can discard the buffer container 12.

At step 114 (FIG. 15), the user removes the basket sieve 14 containing the solid tissue 62 from the sample collection container 16 containing the buffer solution 21, reagent 39 and dislodged cells 64.

At step 116 (FIG. 16), the user places the basket sieve 14 containing the solid tissue 62 into a specimen cup 66 containing formalin. The specimen cup 62 is sealed and sent to a tissue pathology lab. Thereafter the tissue core can undergo traditional tissue processing, for example, to create a glass slide image for the pathologist to make a diagnosis.

At step 118 (FIG. 17), the user seals the sample collection container 16 including the dislodged cells 64, the buffer solution 21 and the reagent 39 for diagnostic testing. The user can seal the sample collection container 16 by attaching the lid 28 that was previously removed from the buffer container 12. The user can send the sealed sample collection container 16 and its contents to a molecular lab for molecular diagnostic testing. At this point the buffer container 12 and the basket sieve 14 have been removed and the sealed sample collection container 16 includes the mixed buffer solution 21, reagent 39 and D-cells 64.

Figure 19:
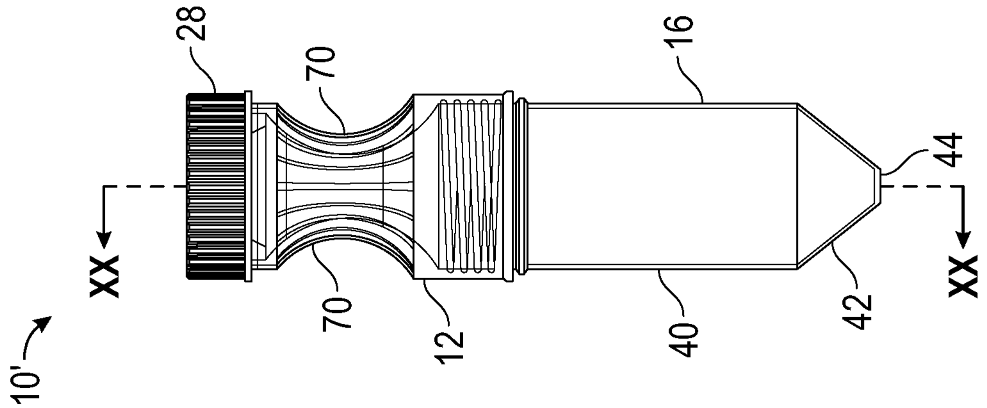
FIG. 19 illustrates a side view of a second example embodiment of a biopsy container apparatus in accordance with the present disclosure.
Figure 20:
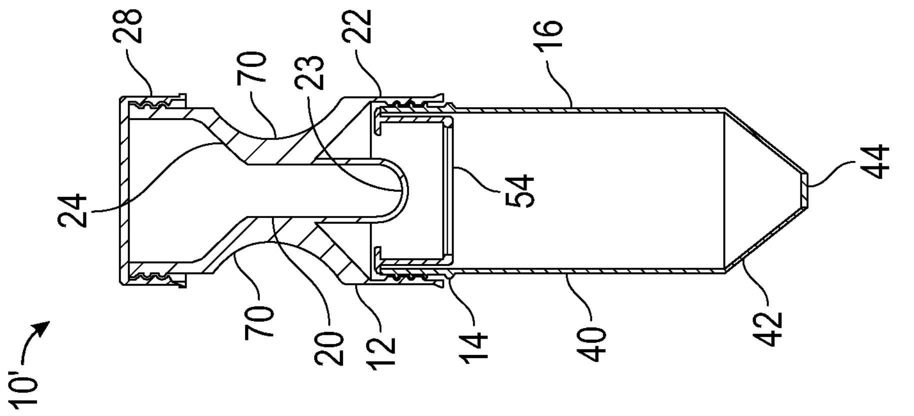
FIG. 20 illustrates a cross-sectional view of the biopsy container apparatus of FIG. 20 taken across section line XX-XX in FIG. 20.

FIGS. 19 and 20 illustrate an alternative second example embodiment of a biopsy container apparatus 10' for recovering solid tissue and D-cells from a biopsy in accordance with the present disclosure. The biopsy container apparatus 10' includes all of the elements of the biopsy container 10, including the basket sieve 14 in the sample collection container 16, besides that the buffer container 12 includes a concave outer surface 70 surrounding the buffer chamber 20 instead of a handle. The concave outer surface 70 reduces the size of the biopsy container apparatus 10' and can be gripped by a user when handling the biopsy container apparatus 10 in accordance with the method 100.

Figure 23:
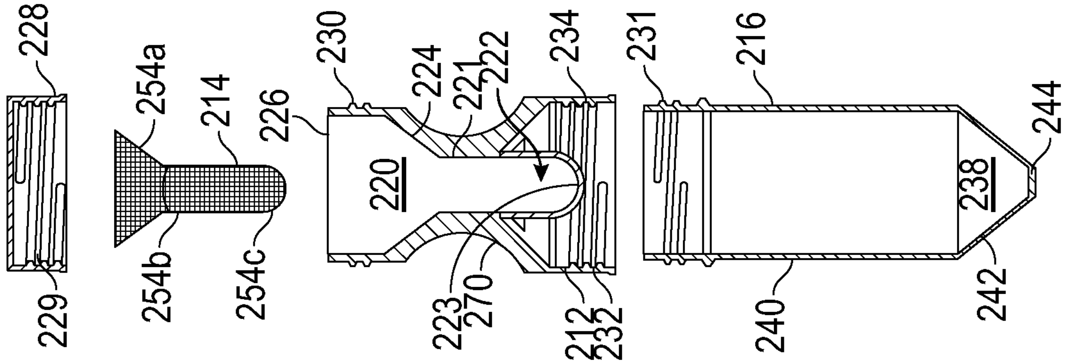
FIG. 23 illustrates an exploded view of the cross-section of the biopsy container apparatus shown in FIG. 22.
Figure 22:
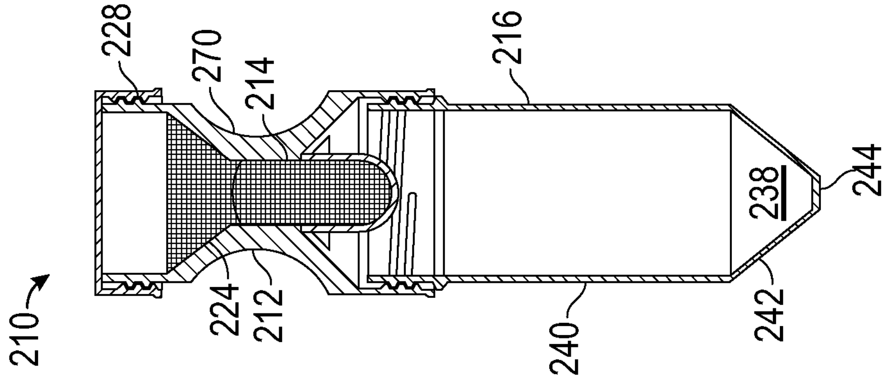
FIG. 22 illustrates a cross-sectional view of the biopsy container apparatus of FIG. 21 taken across section line XXII-XXII in FIG. 21.
Figure 21:
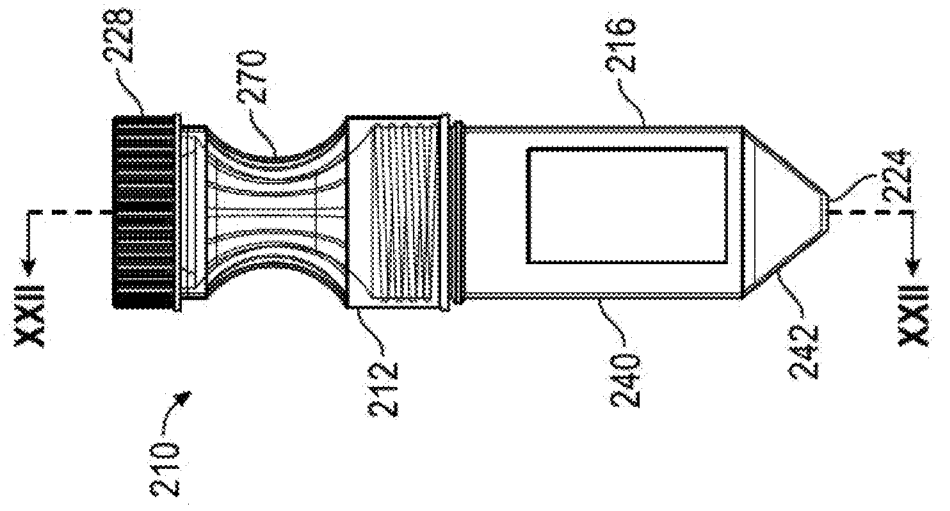
FIG. 21 illustrates a side view of a third example embodiment of a biopsy container apparatus in accordance with the present disclosure.

FIGS. 21 to 23 illustrate another example embodiment of a biopsy container apparatus 210 for recovering solid tissue and D-cells from a biopsy in accordance with the present disclosure. The biopsy container apparatus 210 differs from the biopsy container apparatuses 10, 10' discussed above, for example, in that the biopsy container apparatus 210 includes a sieve container 214 located within the buffer container 12, 212 instead of the sample collection container 16, 216. This ensures that the solid tissue core cannot encounter even trace amounts of reagent (e.g., cell lysing and DNA/RNA preservation solution) stored within the sample collection container 16, 216. This also prevents the solid tissue core from getting "stuck" in the buffer container 12, 212, because instead of relying on the user pouring the solid tissue core out into the basket sieve 14, the solid tissue core is lifted out mechanically when the user lifts the sieve container 214 from the buffer container 212 (step 308 of method 300 described below).

As seen in FIGS. 21 to 23, the biopsy container apparatus 210 includes a buffer container 212, a sieve container 214 and a sample collection container 216, which are three separable elements that can be attached prior to a biopsy and then separated during the method of use disclosed herein. As illustrated, the sieve container 214 is configured for removable attachment with the buffer container 212, and the buffer container 212 is configured for removable attachment with the sample collection container 216. FIGS. 21 and 22 illustrate the buffer container 212, the sieve container 214 and the sample collection container 216 attached together, while FIG. 23 shows the buffer container 212, the sieve container 214 and the sample collection container 216 detached from each other.

The buffer container 212 includes a buffer chamber 220 for storing or receiving buffer solution. The buffer chamber 220 includes an elongated and generally cylindrical portion 221 leading to a bottom edge 223. The portion 221 and the bottom edge 223 of the buffer chamber 220 are sealed and watertight so that the inner space 222 of buffer chamber 220 retains buffer solution. In an embodiment, the buffer chamber 220 is pre-filled with the buffer solution within the inner space 222. In an embodiment, the buffer solution is a sterile phosphate-buffered saline (PBS) buffer solution. In an embodiment, the buffer chamber 220 includes between 2 and 4 mL of buffer solution. In an embodiment, the buffer chamber 220 is pre-filled with approximately 2-4 mL of buffer solution. While PBS is the most likely choice of buffer, any similar buffer solution, such as Buffer Roswell Park Memorial Institute ("RPMI 1640 Media") Buffer Solution, would serve the same purpose.

In the illustrated embodiment, the buffer container 212 includes a funnel to assist a user in depositing a biopsy sample from a core needle into the sieve container 214. More specifically, the buffer container 212 includes a funnel portion 224 leading into the generally cylindrical portion 221 of the buffer chamber 220. The funnel portion 224 flares outwardly from bottom to top. The funnel portion 224 is configured to guide the solid tissue and the D-cells from the biopsy into the sieve container 214 when ejected from a core needle 60, as discussed in more detail below.

In the illustrated embodiment, the buffer container 212 includes a top opening 226 and a lid 228. The lid 228 attaches at or near the top of the funnel portion 224 to cover the top opening 226 and enclose the inner space 222 so that the buffer solution does not spill if the biopsy container apparatus 210 is inverted. The lid 228 can be attached by being screwed onto the buffer container 212 at or near the top of the funnel portion 224, or by another suitable attachment mechanism. In the illustrated embodiment, the lid 228 is configured to attach to both the buffer container 212 and the sample collection container 216, so that a user can remove the lid 228 from the buffer container 12 when beginning use of the biopsy container apparatus 210 and then later place the lid 228 on the sample collection container 216 to seal its contents, as shown for example in FIG. 28.

Figure 28:
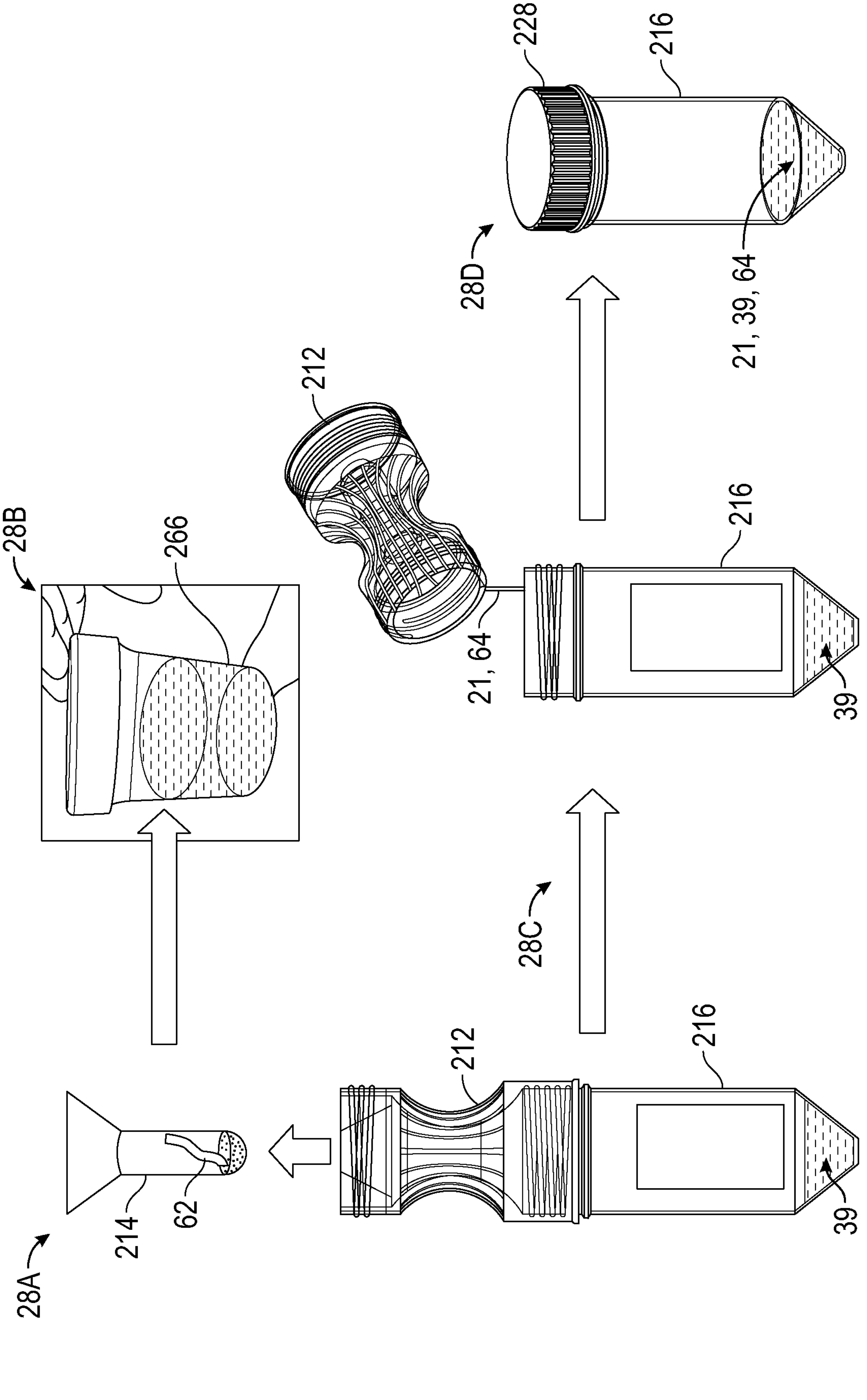

In the illustrated embodiment shown in FIGS. 21 to 23, the lid 228 includes a first attachment mechanism 229 to enable removable attachment to a second attachment mechanism 230 of the buffer container 212. The first attachment mechanism 229 also enables removable attachment to a third attachment mechanism 231 of the sample collection container 216, enabling the lid 228 to be attached to the sample collection container 216 after being removed from the buffer container 212. In the illustrated embodiment, the buffer container 212 also includes a fourth attachment mechanism 232 to enable removable attachment to the third attachment mechanism 231 of the sample collection container 216. In the illustrated embodiment, the inner surface of the lid 228 includes the first attachment mechanism 229, the outer surface of the buffer container 212 includes the second attachment mechanism 230, the outer surface the sample collection container 216 includes the third attachment mechanism 231, and the inner surface of the buffer container 212 includes the fourth attachment mechanism 232. When attached as shown in FIGS. 21 and 22, the first attachment mechanism 229 and the second attachment mechanism 230 create a watertight seal between the buffer container 212 and the lid 228, and the third attachment mechanism 231 and the fourth attachment mechanism 232 create a watertight seal between the buffer container 212 and the sample collection container 216, so that liquid will not spill from the buffer container 212 or the sample collection container 216 if the biopsy container apparatus 210 is inverted. When attached as shown in FIG. 28, the first attachment mechanism 229 and the third attachment mechanism 231 create a watertight seal between the lid 228 and the sample collection container 216 so that liquid will not spill from the sample collection container 216 if inverted.

In the illustrated embodiment, the attachment mechanisms 229, 230, 231, 232 are screw threads. The screw threads of the first attachment mechanism 229 and the fourth attachment mechanism 232 have approximately the same size, and the screw threads of the second attachment mechanism 230 and the third attachment mechanism 231 have approximately the same size. Those of ordinary skill in the art will recognize from this disclosure that other attachment mechanisms are possible.

In the illustrated embodiment, the buffer container 212 includes a concave outer surface 270 and a skirt 234 surrounding the buffer chamber 220. The concave outer surface 270 reduces the size of the biopsy container apparatus 210 and can be gripped by a user when handling the biopsy container apparatus 210 in accordance with the method 300 described below. The skirt 234 includes the fourth attachment mechanism 232 on its inner surface. As seen in FIGS. 22 and 23, the concave outer surface 270 and the skirt 234 both encircle the buffer chamber 220.

FIGS. 22 and 23 show the sieve container 214. In the illustrated embodiment, the sieve container includes a lip portion **254*a*, an intermediate portion 254*b* and a bottom portion 254*c*. One or more of these portions 254*a*, 254*b*, 254*c* can have a shape similar to the corresponding to part of the buffer container 212/buffer chamber 220 so that the sieve container 214 fits into the buffer chamber 220 relatively flush against the inner surfaces of the buffer chamber 220 with little to no space between. Here, the lip portion 254*a* is a funnel portion, similar to the funnel portion 224 of the buffer container 212, which flares outwardly from bottom to top. In the illustrated embodiment, the funnel portion 224 of the buffer container 212 and the lip portion 254*a* of the sieve container 214 have generally the same angle when viewed from the side. In the illustrated embodiment, the intermediate portion 254*b* is a generally cylindrical portion corresponding to the generally cylindrical portion 221 of the buffer chamber 220. In the illustrated embodiment, the bottom portion 254*c* is a generally hemispherical portion corresponding to the generally hemispherical shape of the bottom edge 223 of the buffer chamber 220. By generally conforming the shapes as shown, the sieve container 214 is less likely to be damaged by a core needle during the method of use because the core needle tip is stopped by the harder surfaces (e.g., hard plastic) of the buffer chamber 220, for example, during vigorous swirling of the core needle within the sieve container 214 during step 306 of the method 300 described below. The top of the lip portion 254*a* is also open so that a core needle with solid tissue and D-cells can be inserted therein to deposit the solid tissue and D-cells into the sieve container 214 while the sieve container 214 is located at least partially within the buffer container 212**.

In the illustrated embodiment, each of the lip portion **254*a*, the intermediate portion 254*b* and the bottom portion 254*c* include sieve surfaces configured to pass the D-cells from a biopsy but not solid tissue from the biopsy. The pore size of the sieve surfaces is approximately 350 microns in diameter per pore (the pore aperture size), or within a range of about 80 microns to 500 microns in diameter per pore (the pore aperture size), to allow D-cells to pass through to the buffer chamber 220. In alternative embodiments, one or some surfaces of the lip portion 254*a*, the intermediate portion 254*b* and the bottom portion 254*c* can be sieve surfaces that pass liquids or D-cells, while other surfaces can be other types that do not pass liquids or D-cells. For example, the lip portion 254 can be formed as a non-sieve surface while one or both of the intermediate portion 254*b* and the bottom portion 254*c*** can include sieve surfaces configured to pass D-cells from a biopsy but not solid tissue from the biopsy.

In the illustrated embodiment, the lip portion **254*a* is located on the upper side of the sieve container 214 and rests on the buffer container 212 to suspend the sieve container 214 at least partially within the buffer chamber 220. In an embodiment, the lip portion 254*a* that rests on a surface of the buffer container 212 to suspend the sieve container 214** can be made in other shapes and sizes alternative to the funnel shape shown.

As seen in FIG. 22, the sieve container 214 is suspended at least partially within the buffer chamber 220 when the biopsy container apparatus 210 is assembled. In the illustrated embodiment, the sieve container 214 is configured to rest on an inner surface of the buffer container 212 and extend into the buffer chamber 220. Here, the lip portion **254*a* rests on the funnel portion 224 of the buffer container 212, such that the intermediate portion 254*b* of the sieve container 214 extends into the generally cylindrical portion 221 of the buffer chamber 220. The width or diameter of the intermediate portion 254*b* is therefore slightly smaller than the diameter of the cylindrical portion 221 of the buffer chamber 220. In an embodiment, the sieve container 214 can include loop-like or hook-like vertical members to assist a user in lifting the sieve container 214 upward to remove the sieve container 214 (and the tissue it carries) from the buffer container 212 during use. As seen in FIG. 28, the sieve container 214 is sized and shaped to be sealed within a corresponding specimen cup 266** and sent to a tissue pathology lab.

The sample collection container 216 includes a reagent chamber 238 for storing or receiving a reagent. In the illustrated embodiment, the sample collection container 216 includes an upper portion 240 and a lower portion 242, with the reagent chamber 238 located within and/or formed by the lower portion 242. The bottom edge 244 of the sample collection container 216 is sealed and watertight so that the reagent chamber 238 retains the reagent. In an embodiment, the reagent chamber 238 is pre-filled with the reagent within the inner space. In an embodiment, the reagent is a solution for lysing cells and preserving nucleic acids that is approximately 2× the normal concentration of an off-the-shelf cell lysing reagent. In an embodiment, the reagent is Zymo DNA/RNA Shield™ reagent, or an equivalent for lysing cells and preserving nucleic acids which is 2× the normal concentration defined by and provided by Zymo. In an embodiment, the reagent chamber 38 includes between 2 and 4 mL of reagent. In an embodiment, the reagent chamber 238 is pre-filled with 2-4 mL of double-concentration cell lysis/nucleic acid stabilization reagent. In an embodiment, the reagent chamber 238 includes a first amount of reagent, and the buffer chamber 220 includes a second amount of buffer solution that is approximately equal in volume to the first amount of reagent.

As seen in FIG. 22, when the buffer container 212, the sieve container 214 and the sample collection container 216 are attached to each other, the sieve container 214 is suspended within the buffer chamber 220 of the buffer container 212. That is, sieve container 214 is located at least partially within the buffer chamber 220. In an embodiment, the buffer chamber 220 is prefilled with a buffer solution, and the bottom portion 254*c* and at least part of the intermediate portion 254*b* extend into the buffer solution before the solid tissue and D-cells are inserted into the sieve container 214. That is, the sieve container 214 is at least partially submerged in the buffer solution in the buffer container 220.

The dimensions of a biopsy container apparatus 210 in accordance with the present disclosure can vary. In the illustrated embodiment, the total height of the biopsy container apparatus 210 is approximately 12.4 cm, the height of the sample collection container 216 is approximately 7.6 cm, the outer diameter of the upper portion 240 of the sample collection container 216 is approximately 3.0 cm, and the outer diameter of the lid 228 is approximately 3.3 cm. The buffer chamber 220 has an approximate inner diameter of 10 mm and an approximate height of 30 mm, and the width or diameter of the intermediate portion 254*b* of the sieve container 214 is slightly less than approximately 2.7 cm so that the sieve container 214 fits into the buffer chamber 220. Those of ordinary skill in the art will recognize from this disclosure that these dimensions are an example only and can change with different embodiments.

FIG. 24 shows an example embodiment of a method 300 of recovering solid tissue and D-cells from a biopsy using a biopsy container apparatus 210 in accordance with the present disclosure. FIGS. 25 to 28 illustrate various steps of the method 300. Those of ordinary skill in the art will recognize from this disclosure that certain steps can be added, removed or altered without departing from the spirit and scope of the present disclosure.

In an embodiment, at the beginning of the method 300, the biopsy container apparatus 210 is provided as a single unit as shown in FIGS. 21 and 22, with (i) the buffer container 212 pre-filled with buffer solution, (ii) the sample collection container 216 pre-filled with reagent, (iii) the buffer container 212 attached to the sample collection container 216, and (iv) the sieve container 214 sealed within the buffer container 212 by the lid 228. In an alternative embodiment, the biopsy container apparatus 210 can be provided without the buffer solution and/or reagent, which can be added by the user before or as the method 300 is performed.

At step 302, a user (e.g., interventional radiologist, technician, or other clinical user) uses a core needle 60 to harvest an image guided biopsy from a patient with suspicious mass lesion inside his or her body (e.g., liver, lung, kidney, etc). The core needle 60 removes both solid tissue 62 and dislodged cells 64 (D-cells) from the patient.

At step 304, (FIG. 25), the user removes the lid 228 from the buffer container 212. The lid 228 can be set aside and later reused to seal the sample collection container 216 at step 316.

Figure 27:
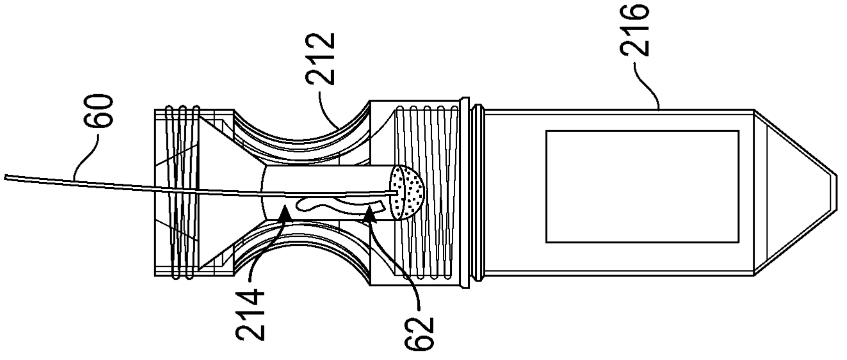
FIGS. 25 to 28 illustrate example embodiments of the steps of the method of FIG. 24.
Figure 26:
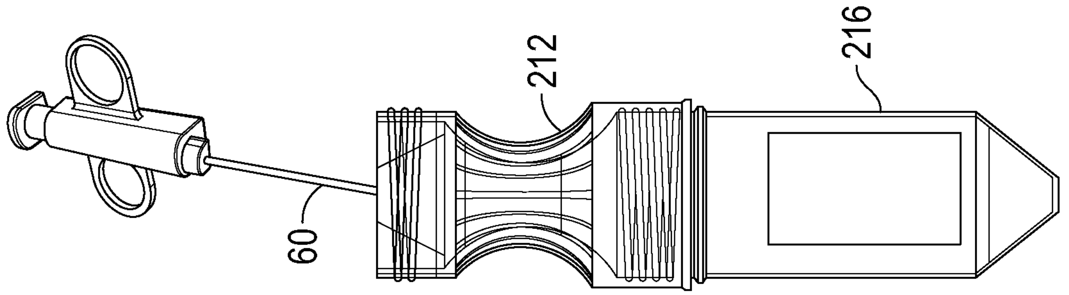
Figure 25:
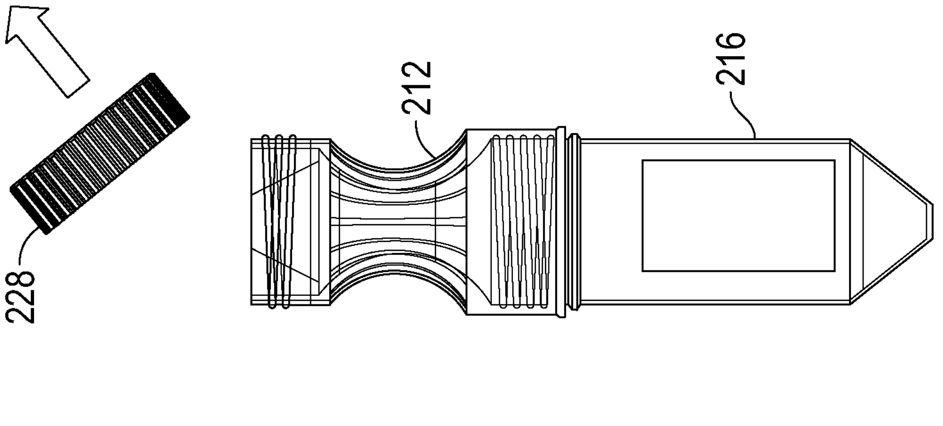

At step 306 (FIGS. 26 and 27), the user deposits the contents of the core needle 60 including the solid tissue 62 and the D-cells 64 into the sieve container 214 while the sieve container 214 is located within the buffer chamber 220 of the buffer container 212. The user may swirl the CNB needle tip to deposit the harvested tissue sample by moving the core needle 60 in a roughly circular fashion. The shape of the funnel portion 224 and the lip portion 254*a* make it easy for the user to spatially coordinate the CNB needle tip and the target area and provides a convenient way to for the user to place the tip of the core needle 60 (and therefore the tissue sample) near or into the sieve container 214. That is, the funnel shapes of the funnel portion 224 and the lip portion 254*a* makes it easier to fit the core needle 60 into the sieve container 214 since the user's hand is approximately eight (8) inches away from the needle tip (holding the handle; not the tip), and the other hand is holding the buffer container 212 at the concave outer surface 270 or a conventional tray or rack in which the buffer container 212 is placed (not pictured) or otherwise unavailable and generally not used to guide the tip of the needle 60. As seen in FIG. 27, when the user deposits the contents of the core needle 60 into the sieve container 214, the sieve container 214 retains the solid tissue 62, while the D-cells 64 and the buffer solution 21 flow through the sieve surfaces of the sieve container 214 and mix.

At step 308 (FIG. 28 at 28A), the user removes the sieve container 214 containing the solid tissue 62 from the buffer container 212, while the buffer container 212 retains the buffer solution 21 and dislodged cells 64. In the illustrated embodiment, the user removes the sieve container 214 by lifting the sieve container 214 upwards out of the buffer chamber 220.

At step 310 (FIG. 28 at 28B), the user places the sieve container 214 containing the solid tissue 62 into a specimen cup 266 containing formalin. The specimen cup 266 is sealed and sent to a tissue pathology lab. Thereafter the solid tissue 62 can undergo traditional tissue processing, for example, to create a glass slide image for the pathologist to make a diagnosis. In an embodiment, the specimen cup 266 is sent to a pathology lab for FFPE (e.g., embedding into paraffin and cut into sections on a microtome).

At step 312 (FIG. 28 at 28C), the user removes the buffer container 212 from the sample container 216. The user removes the buffer container 212 from the sample collection container 216, for example, by detaching (e.g., unscrewing) the third attachment mechanism 231 and the fourth attachment mechanism 232.

At step 314 (FIG. 28 at 28C), the user pours the contents of the buffer chamber 220 (the D-cells 64 and the buffer solution 21) into the sample collection container 216. The buffer solution 21 and the D-cells 64 mix with the reagent 39 in the reagent chamber 238 of the sample collection container 216. Since the reagent is 2× concentrated within the reagent chamber 238, the additional volume of buffer solution 21 and dislodged cells 64 restores the reagent concentration to normal. In an embodiment, the reagent is pre-filled cell lysing and DNA/RNA preservation solution. Since the sieve container 214 is removed at this point, there is no way that the solid tissue 62 can encounter even trace amounts of cell lysing and DNA/RNA preservation solution from the sample collection container 216.

At step 316 (FIG. 28 at 28D), the user seals the sample collection container 216 including the dislodged cells 64, the buffer solution 21 and the reagent 39 for diagnostic testing. The user can seal the sample collection container 216 by attaching the lid 228 that was previously removed from the buffer container 212. The user can send the sealed sample collection container 216 and its contents to a molecular lab for molecular diagnostic testing. At this point the buffer container 212 and the sieve container 214 have been removed and the sealed sample collection container 16 includes the mixed buffer solution 21, reagent 39 and D-cells 64.

Those of ordinary skill in the art will recognize from this disclosure that the features of any of the embodiments of the biopsy container apparatuses 10, 10', 210 can be added to any of the other embodiments of the biopsy container apparatuses 10, 10', 210, and similarly that certain steps of the method 100 and the method 300 can be combined or rearranged without departing from the spirit and scope of the present disclosure.

The embodiments described herein provide improved apparatuses and methods for segregating tissue samples for multiple diagnostic modalities. An advantage of the disclosed apparatuses and methods is that D-cells can be collected at the site of the procedure, in an easy to perform process that almost completely eliminates pre-analytic variation and more importantly, before exposure to formalin fixation. This front-end approach, where the collection and stabilization occurs before fixation, is in contrast to other proposed biopsy substrate shortage solutions that seek to improve the substrate after it has already been fixed in formalin and damaged (back-end approaches). Prototype testing has shown that the specimen collected as D-cells by using this method result in more than sufficient amounts of nucleic acids, that are also of high quality, for molecular studies.

It should be understood that various changes and modifications to the apparatuses and methods described herein will be apparent to those skilled in the art and can be made without diminishing the intended advantages.

General Interpretation of Terms

In understanding the scope of the present invention, the term "comprising" and its derivatives, as used herein, are intended to be open-ended terms that specify the presence of the stated features, elements, components, groups, and/or steps, but do not exclude the presence of other unstated features, elements, components, groups, integers and/or steps. The foregoing also applies to words having similar meanings such as the terms, "including", "having" and their derivatives. Also, the terms "part," "section," or "element" when used in the singular can have the dual meaning of a single part or a plurality of parts.

The term "configured" as used herein to describe a component, section or part of a device includes hardware that is constructed to carry out the desired function.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such features. Thus, the foregoing descriptions of the embodiments according to the present invention are provided for illustration only, and not for the purpose of limiting the invention as defined by the appended claims and their equivalents.

What is claimed is:

1. A biopsy container apparatus for recovering solid tissue and dislodged cells ("D-cells") from a biopsy, the biopsy container apparatus comprising:

a buffer container including a buffer chamber with a bottom that is sealed and watertight;

a sieve container located at least partially within the buffer container, the sieve container including a sieve surface configured to pass the D-cells from the biopsy but not the solid tissue from the biopsy into the buffer chamber; and a sample collection container removably attached to the buffer container, the sample collection container including a reagent chamber.

2. The biopsy container apparatus of claim 1, wherein the buffer container includes a funnel portion configured to guide the solid tissue and the D-cells from the biopsy into the sieve container.

3. The biopsy container apparatus of claim 1, wherein the sieve container includes a lip portion configured to suspend the sieve container at least partially within buffer chamber.

4. The biopsy container apparatus of claim 1, wherein the sieve container includes a funnel portion configured to rest on a portion of the removable buffer container to suspend the sieve container at least partially within the buffer chamber.

5. The biopsy container apparatus of claim 1, wherein the buffer container includes an inner surface with a first attachment mechanism, the sample collection container includes an outer surface with a second attachment mechanism, and the buffer container is removably attached to the sample collection container by cooperation between the first attachment mechanism and the second attachment mechanism.

6. The biopsy container apparatus of claim 5, wherein the first attachment mechanism and the second attachment mechanism include corresponding threads enabling the buffer container to be screwed onto the sample collection container.

7. The biopsy container apparatus of claim 1, comprising a lid that fits both the sample collection container and the buffer container.

8. The biopsy container apparatus of claim 1, wherein the buffer container is pre-filled with a solution in the chamber, and the sample collection container is pre-filled with a reagent in the reagent chamber.

9. The biopsy container apparatus of claim 8, wherein the buffer container includes between 2 and 4 mL of solution, and the sample collection container includes between 2 and 4 mL of reagent.

10. The biopsy container apparatus of claim 1, wherein the sample collection container includes a second bottom that is sealed and watertight.

11. A biopsy container apparatus for recovering solid tissue and dislodged cells ("D-cells") from a biopsy, the biopsy container apparatus comprising:

a buffer container including a top opening and a buffer chamber with a bottom that is sealed and watertight;

a sieve container located within the buffer container and configured to be lifted out of the buffer container through the top opening, the sieve container including a sieve surface positioned and configured to allow the D-cells but not the solid tissue from the biopsy to pass into the buffer container while the sieve container is located within the buffer container; and a sample collection container removably attached to the buffer container and including a reagent chamber.

12. The biopsy container apparatus of claim 11, wherein the buffer container includes a lid, and the sieve container is located between the lid and the buffer container.

13. The biopsy container apparatus of claim 11, wherein the sieve container is at least partially submerged in the solution in the removable buffer container.

14. The biopsy container apparatus of claim 11, wherein the sieve container includes a lip portion configured to suspend the sieve container at least partially within the buffer container.

15. A method of recovering solid tissue and dislodged cells ("D-cells") from a biopsy using a biopsy container apparatus including a buffer container, a sieve container and a sample collection container, the method comprising:

depositing the solid tissue and the D-cells from the biopsy into the sieve container while the sieve container is located at least partially within a buffer chamber of the buffer container which has a bottom that is sealed and watertight and contains a solution;

placing the sieve container with the solid tissue into a sealed container for tissue processing;

pouring the D-cells and the solution from the buffer container into the sample collection container which contains a reagent; and sealing a mixture including the D-cells, the solution and the reagent for diagnostic testing.

16. The method of claim 15, comprising depositing the solid tissue and the D-cells from a core needle into the sieve container.

17. The method of claim 15, wherein sealing a mixture including the D-cells, the solution and the reagent includes sealing the mixture within the sample collection container.

18. The method of claim 15, comprising receiving the biopsy container apparatus with the buffer container, the sieve container and the sample collection container attached together.

19. The method of claim 18, comprising receiving the biopsy container apparatus with the sample collection container pre-filled with the reagent, the sieve container located at least partially within the buffer container, and the buffer container pre-filled with a solution.

20. The method of claim 15, comprising removing a lid from the buffer container before depositing the solid tissue and the D-cells from the biopsy into the sieve container, and wherein sealing the mixture including the D-cells, the solution and the reagent for the diagnostic testing includes sealing the D-cells, the solution and the reagent within the sample collection container using the lid.

* * * * *